United States Patent
Sano et al.

(10) Patent No.: US 7,316,653 B2
(45) Date of Patent: Jan. 8, 2008

(54) BLOOD PRESSURE MEASURING DEVICE

(75) Inventors: Yoshihiko Sano, Kyoto (JP); Takefumi Nakanishi, Nagaokakyo (JP); Takahide Tanaka, Otsu (JP); Minoru Taniguchi, Uji (JP); Tomonori Inoue, Kyoto (JP); Hiroya Nakanishi, Kyoto (JP); Yukiya Sawanoi, Nara (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/062,964

(22) Filed: Feb. 23, 2005

(65) Prior Publication Data

US 2005/0192501 A1    Sep. 1, 2005

(30) Foreign Application Priority Data

Feb. 27, 2004    (JP)    ............... 2004-054362

(51) Int. Cl.
*A61B 5/02*    (2006.01)
(52) U.S. Cl. ............. 600/499; 600/485; 600/490
(58) Field of Classification Search .......... 600/499
See application file for complete search history.

(56) References Cited

U.S. PATENT DOCUMENTS

| | | | | |
|---|---|---|---|---|
| 5,069,219 | A * | 12/1991 | Knoblich | 600/492 |
| 5,111,539 | A * | 5/1992 | Hiruta et al. | 4/661 |
| 5,218,955 | A * | 6/1993 | Gueret | 601/123 |
| 5,218,966 | A * | 6/1993 | Yamasawa | 600/490 |
| 5,735,798 | A | 4/1998 | Shinohara et al. | |
| 5,778,879 | A * | 7/1998 | Ota et al. | 600/485 |
| 6,413,224 | B1 | 7/2002 | Ogura et al. | |
| 6,428,124 | B1 * | 8/2002 | Bluth et al. | 312/194 |
| 6,872,182 | B2 * | 3/2005 | Kato et al. | 600/490 |
| 2003/0078507 | A1 * | 4/2003 | Sadritabrizi | 600/499 |

FOREIGN PATENT DOCUMENTS

DE    2837707    *  8/1978

(Continued)

OTHER PUBLICATIONS

European Search Report dated Jun. 28, 2005, directed to corresponding foreign application.

(Continued)

*Primary Examiner*—Charles A. Marmor, II
*Assistant Examiner*—Patricia C Mallari
(74) *Attorney, Agent, or Firm*—Morrison & Foerster LLP

(57) ABSTRACT

A blood pressure monitor includes a main unit casing placed on a table, a living body insert portion casing of an approximately cylindrical shape, positioned on the main unit casing in a non-use state and having a cuff arranged on its inner peripheral surface, the cuff having a hollow portion to which an upper arm of a subject is inserted, and a connection mechanism for connecting the living body insert portion casing with the main unit casing in a movable manner such that, upon application of the cuff to the subject, the living body insert portion casing can move to come closer to the subject than the main unit casing. Thus, a blood pressure monitor provided with an automatic cuff winding mechanism enabling measurement of blood pressure with high accuracy, not giving unnecessary pain to the subject, and allowing measurement with an unconstrained posture can be provided.

13 Claims, 20 Drawing Sheets

FOREIGN PATENT DOCUMENTS

| | | | |
|---|---|---|---|
| DE | 283 77 07 A1 * | 3/1980 |
| DE | 2837707 * | 3/1980 |
| DE | 2837707 A1 | 3/1980 |
| EP | 0415288 A1 | 3/1991 |
| EP | 0700657 A1 | 3/1996 |
| JP | 55-029303 A | 3/1980 |
| JP | 57-180939 | 11/1982 |
| JP | 57-180940 | 11/1982 |
| JP | 58-117604 | 8/1983 |
| JP | 63-305841 * | 12/1988 |
| JP | 63305841 | 12/1988 |
| JP | 2-135003 | 11/1990 |
| JP | 10-314123 | 12/1998 |
| JP | 10-314125 | 12/1998 |
| JP | 2594576 | 2/1999 |
| JP | 2000-041958 A | 2/2000 |
| JP | 2002-159351 | 6/2002 |
| JP | 2004-254882 | 9/2004 |
| JP | 2005-230175 | 9/2005 |
| JP | 2005-237802 A | 9/2005 |

OTHER PUBLICATIONS

Japanese Office Action mailed Feb. 21, 2006, directed to counterpart JP Application No. 2004-054362.

Chinese Office Action mailed on Sep. 22, 2006 for Chinese Application No. 2005-10052504.9 filed on Feb. 28, 2005, 8 pages.

* cited by examiner

PRESSURE VALUE WITHIN AIR BAG
LABEL OF SUBJECT
TIME

WARNING MARK

PRESSURE VALUE WITHIN AIR BAG
LABEL OF SUBJECT
TIME

WARNING MARK

BLOOD PRESSURE MEASURING DEVICE

BACKGROUND OF THE INVENTION

1. Field of the Invention

The present invention relates to a blood pressure measuring device, and more particularly to a blood pressure measuring device provided with an automatic cuff winding mechanism for automatically winding a cuff around a living body.

2. Description of the Background Art

To measure a blood pressure value, generally, a cuff provided with a living body pressing fluid bag for pressing an artery located within the living body is wound around the body surface, and arterial pressure pulse waves caused in the artery by inflation/deflation of the living body pressing fluid bag are detected to measure the blood pressure value. Here, the cuff refers to a band-shaped structure having a bladder, which can be wound around a portion of a living body, for use in measurement of arterial pressure of an upper limb, a lower limb or the like by introducing fluid such as gas or liquid into the bladder. Thus, the cuff represents the concept including the living body pressing fluid bag as well as a unit for winding the living body pressing fluid bag around the living body.

In a conventional blood pressure measuring device (hereinafter, also simply referred to as a "blood pressure monitor"), the cuff was wound around the living body by a subject or the like, so that there occurred variation in the cuff winding strength, which caused variation in the blood pressure values measured. Thus, in recent years, blood pressure monitors provided with an automatic cuff winding device have become widespread, which enables automatic winding of the cuff around the living body. With the blood pressure monitor provided with the automatic cuff winding device, constant winding strength is reproduced for each time of measurement, which ensures stable and accurate measurement and also eliminates the burdensome, cuff winding job.

A blood pressure monitor provided with an automatic cuff winding mechanism generally has a hollow opening at a prescribed position of the main unit case into which a portion of the living body is inserted, and a cuff for securing the living body by pressing is disposed on the inner peripheral surface of the hollow opening. The automatic cuff winding mechanism housed in the main unit case is used to wind the cuff around an upper arm, for example, inserted into the hollow opening, to measure a blood pressure value.

The blood pressure monitors each provided with an automatic cuff winding mechanism as described above are disclosed, e.g., in Japanese Patent Laying-Open Nos. 10-314123, 10-314125, and Japanese Utility Model Laying-Open No. 02-135003. The blood pressure monitors disclosed therein, however, pose the following problems.

Firstly, in each of the blood pressure monitors provided with automatic cuff winding mechanisms disclosed in Japanese Patent Laying-Open Nos. 10-314123 and 10-314125, a living body insert portion including a hollow opening into which an arm is inserted is integral with a main unit incorporating a cuff winding mechanism, thereby restricting the posture allowed to a subject at the time of measurement. The posture of a subject upon measurement varies depending on the body type of the subject, the height of a table on which the blood pressure monitor is placed, the height of a chair on which the subject sits, and others. Thus, if the inclination angle of the living body insert portion and the inclination angle of the subject's arm inserted do not match, there occurs a gap between the cuff and the arm, in which case the arm cannot be pressed uniformly, leading to degradation of accuracy in measurement. Further, the subject would feel pain, since he/she needs to keep a constrained posture during the measurement.

In the blood pressure monitor provided with an automatic cuff winding mechanism disclosed in Japanese Utility Model Laying-Open No. 02-135003, the cuff winding mechanism provided in the living body insert portion is supported by a plate spring or a plurality of coil springs, to allow swinging of the winding mechanism itself The hollow opening provided at the living body insert portion, however, is integral with the main unit, so that the angle of insertion of the arm is restricted at the mouth of the living body insert portion, again restricting the posture of a subject at the time of measurement. Although the degree of freedom of the posture upon measurement is somewhat improved compared to the automatic cuff winding mechanism disclosed in Japanese Patent Laying-Open Nos. 10-314123 and 10-314125, the problem has not been solved completely. Further, since the winding mechanism is elastically biased with the plate spring or the coil springs, large flexure of the springs will apply load on the cuff by their elastic force, causing degradation of measurement accuracy.

As a blood pressure monitor provided with an automatic cuff winding mechanism attempting to solve the above-described problems, one as shown in FIG. 27 is known. In the blood pressure monitor 100E shown in FIG. 27, a main unit 110 and a living body insert portion 140 are formed in two pieces, and are connected in a pivotable manner via a pivot 145 provided on the rear end of main unit 110. With this configuration, living body insert portion 140, located on top of main unit 110 in a non-use state, is tilted backward (in a direction shown by an arrow H in the figure) as a subject 300 inserts the arm, and the inclination angle of living body insert portion 140 is adjusted in accordance with the subject's posture upon measurement. This enables accurate measurement of the blood pressure value, without restricting the posture of the subject to cause pain.

The blood pressure monitor shown in FIG. 27, however, poses an additional problem as follows. In blood pressure monitor 100E, as shown in FIG. 27, upon applying the cuff on the upper arm 320, living body insert portion 140 is tilted backward (in the direction of arrow H in the figure). This means that living body insert portion 140 moves with respect to main unit 110 in a direction opposite to the side of subject 300. As such, subject 300 is required to slouch forward to follow the movement of living body insert portion 140. Thus, as shown in FIG. 27, in order for subject 300 to apply the cuff on upper arm 320, he/she needs to slouch forward on the side of desk 210 and keep the relevant posture for several tens of seconds during the measurement. This makes subject 300 suffer pain until the end of measurement.

If the subject wants to stand erect during the measurement, instead of slouching forward, he/she needs to move blood pressure monitor 100E itself to the front end of desk 210, or move chair 220 to come closer to desk 210. Such adjustment while upper arm 320 is being inserted in the hollow opening is very tiresome, thereby imposing an unnecessary burden on subject 300.

SUMMARY OF THE INVENTION

An object of the present invention is to provide a blood pressure measuring device provided with an automatic cuff winding mechanism that enables measurement of a blood pressure value with high accuracy, hardly causes pain to a subject during the measurement, and allows the subject to keep an unconstrained posture during the measurement.

The blood pressure measuring device according to the present invention includes: a first enclosure rested on a table; a second enclosure located on the first enclosure in a non-use state and having a cuff arranged on its inner peripheral surface, the cuff having a hollow opening to which a portion of a living body of a subject is inserted; and a connection mechanism for connecting the second enclosure with the first enclosure in a movable manner such that, upon application of the cuff to the subject, the second enclosure can move to come closer to the subject than the first enclosure.

Preferably, the blood pressure measuring device according to the present invention further includes an inclination level detecting portion for detecting an inclination level of the second enclosure.

Still preferably, the blood pressure measuring device according to the present invention further includes an informing portion for informing the subject of a result of determination as to whether the inclination level of the second enclosure detected by the inclination level detecting portion is within a predetermined range.

Still preferably, the blood pressure measuring device according to the present invention further includes a control unit for determining whether the inclination level of the second enclosure detected by the inclination level detecting portion is within a predetermined range, and when it is out of the predetermined range, for controlling to terminate a measurement operation when it is already in progress, and not to enter a measurement operation when it is yet to be started.

In the blood pressure measuring device according to the present invention, the inclination level detecting portion may be one for detecting an inclination angle of the second enclosure with respect to a horizontal plane.

Alternatively, in the blood pressure measuring device according to the present invention, the inclination level detecting portion may be one for detecting an inclination angle of the second enclosure with respect to the first enclosure.

Yet alternatively, in the blood pressure measuring device according to the present invention, the inclination level detecting portion may be one for detecting an amount of movement of the second enclosure with respect to the first enclosure.

In the blood pressure measuring device according to the present invention, the connection mechanism may be formed of a pivot connection mechanism including a pivot that supports the second enclosure with respect to the first enclosure in a pivotable manner.

In the blood pressure measuring device according to the present invention, the pivot is preferably provided at an end of the first enclosure on the subject side.

In the blood pressure measuring device according to the present invention, it is preferable that torque required to be applied to the pivot to move the second enclosure is smaller than torque that is imposed on the pivot in accordance with a change in pressure of the cuff during the measurement.

In the blood pressure measuring device according to the present invention, the pivot connection mechanism preferably includes at least one of a dumper and a friction spring for suppressing abrupt pivotal movement of the second enclosure.

In the blood pressure measuring device according to the present invention, the pivot connection mechanism preferably further includes a bias portion for biasing the second enclosure in a direction away from the first enclosure in a non-use state, and a locking portion for locking the second enclosure with the first enclosure in opposition to bias force of the bias portion in the non-use state.

In the blood pressure measuring device according to the present invention, the connection mechanism may be formed of a slide connection mechanism that supports the second enclosure with respect to the first enclosure in a slidable manner.

According to the present invention, the subject can take an unforced posture during the measurement, without suffering pain, so that accurate and stable measurement of the blood pressure value becomes possible.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention will be described in detail with reference to the drawings.

First Embodiment

A blood pressure monitor according to the present embodiment detects arterial pressure pulse waves by pressing an upper arm of a subject, to measure a blood pressure value. The blood pressure monitor of the present embodiment is provided with an automatic cuff winding mechanism to wind a cuff around the upper arm.

Firstly, a basic configuration of the blood pressure monitor of the present embodiment will be explained with reference to FIGS. 1-3.

Figure 1:
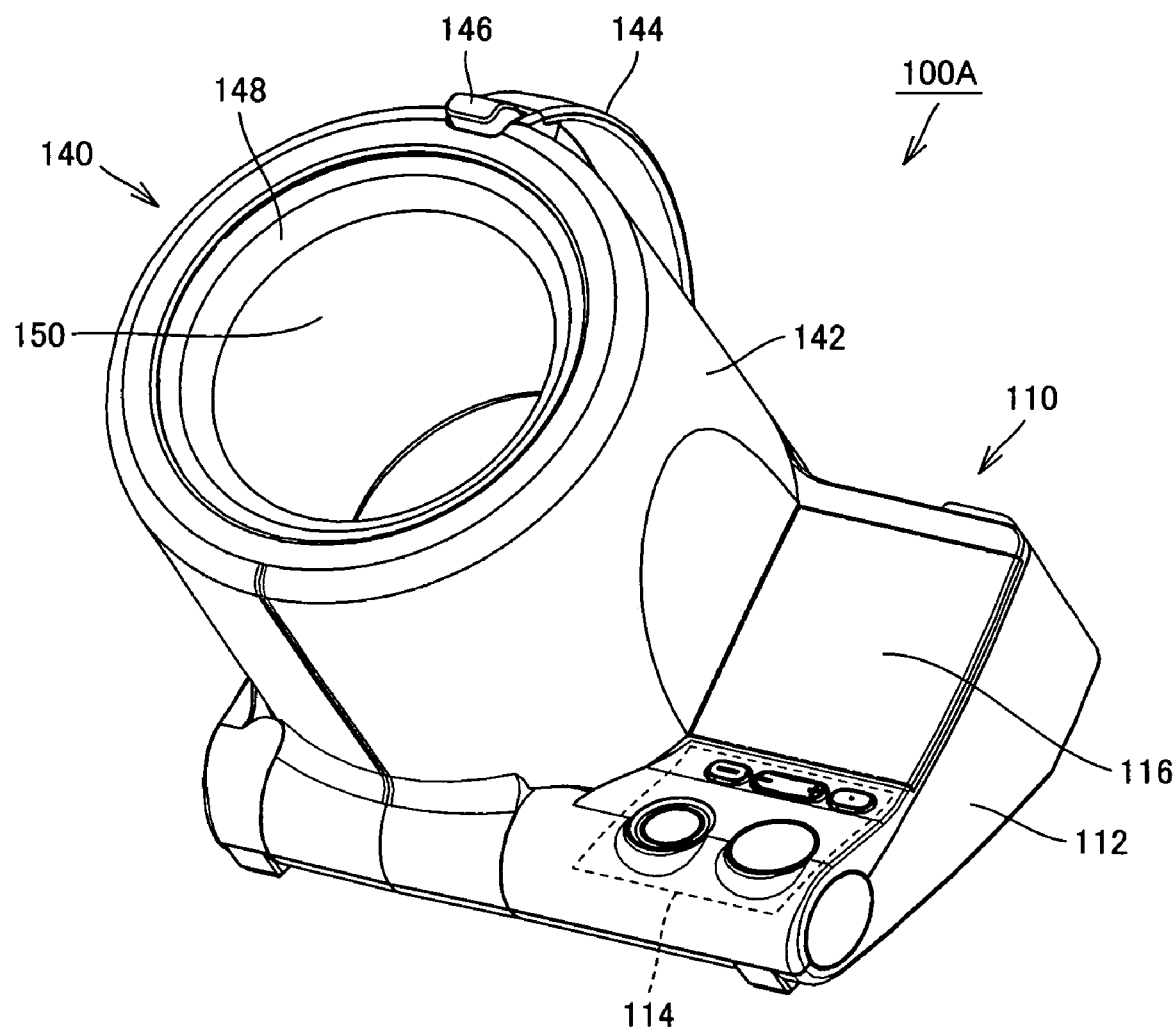
FIG. 1 is a perspective view, as seen from upper right, showing an external structure of a blood pressure monitor according to a first embodiment of the present invention.
Figure 2:
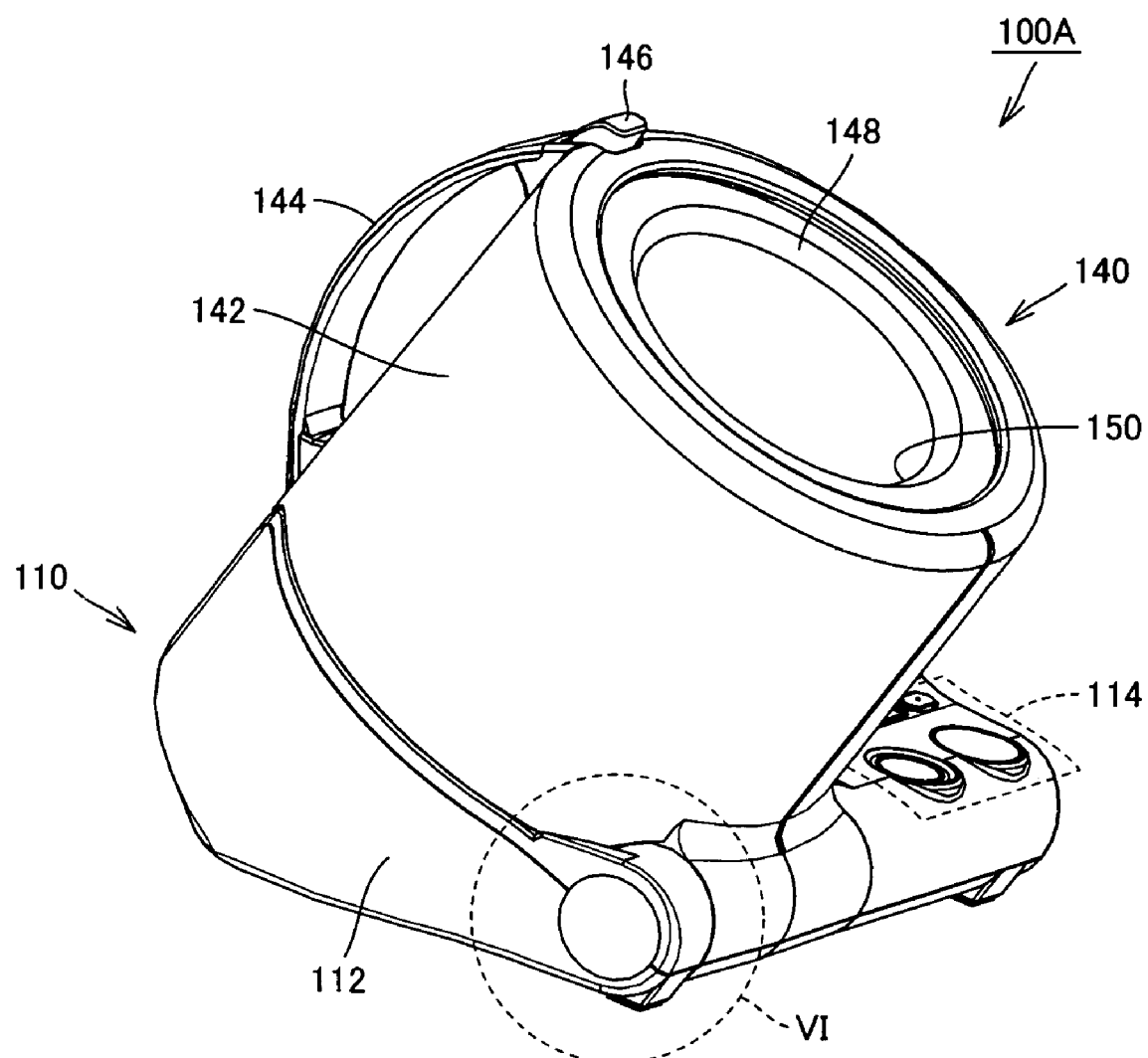
FIG. 2 is a perspective view, as seen from upper left, showing the external structure of the blood pressure monitor of the first embodiment.

As shown in FIGS. 1 and 2, the blood pressure monitor 100A according to the present embodiment primarily includes a main unit 110 placed on a table or the like, and a living body insert portion 140 having a hollow opening 150 to which a portion of a living body (an upper arm in the case of blood pressure monitor 100A of the present embodiment) of a subject is inserted. Main unit 110 is covered with a casing for the main unit (hereinafter, referred to as the "main unit casing") 112 that is a first enclosure, and living body insert portion 140 is covered with a casing for the living body insert portion (hereinafter, referred to as the "living body insert portion casing") 142 that is a second enclosure.

Provided on the upper surface of main unit 110 is a control portion 114 having various buttons arranged therein, which include a power supply button for turning the power on, a measurement button for starting a measurement operation, a display portion control button for controlling a display portion, and others. A display portion 116 is provided on another part of the upper surface of main unit 110, for displaying a result of the measurement, operating guides and others. An elbow rest 119 for resting the elbow when the subject takes a posture for measurement is provided at a prescribed position on the upper surface of main unit 110, adjacent to control portion 114 and display portion 116 (see FIG. 9). This elbow rest 119 is, for example, a depression provided on the upper surface of main unit casing 112.

Living body insert portion 140 is connected to main unit 110 in a pivotable manner by means of a pivot connection mechanism including a pivot. Specifically, the pivot arranged within main unit casing 112 to the front end of main unit 110 facing the subject connects main unit casing 112 with living body insert portion casing 142 in a pivotable manner.

Living body insert portion 140 includes a cuff arranged on the inner peripheral surface of living body insert portion casing 142 of an approximately cylindrical shape, and a cuff cover 148 attached to living body insert portion casing 142 to cover the cuff. A handle 144 is also provided at a prescribed position on the outer peripheral surface of living body insert portion casing 142, which is used by a subject to pivotally move living body insert portion 140. Further, an unlocking button 146 is provided in the vicinity of handle 144, which is used to allow pivotal movement of living body insert portion casing 142 rested on main unit 110. Unlocking button 146 and an unlocking/locking mechanism cooperating therewith will be described later.

Figure 3:
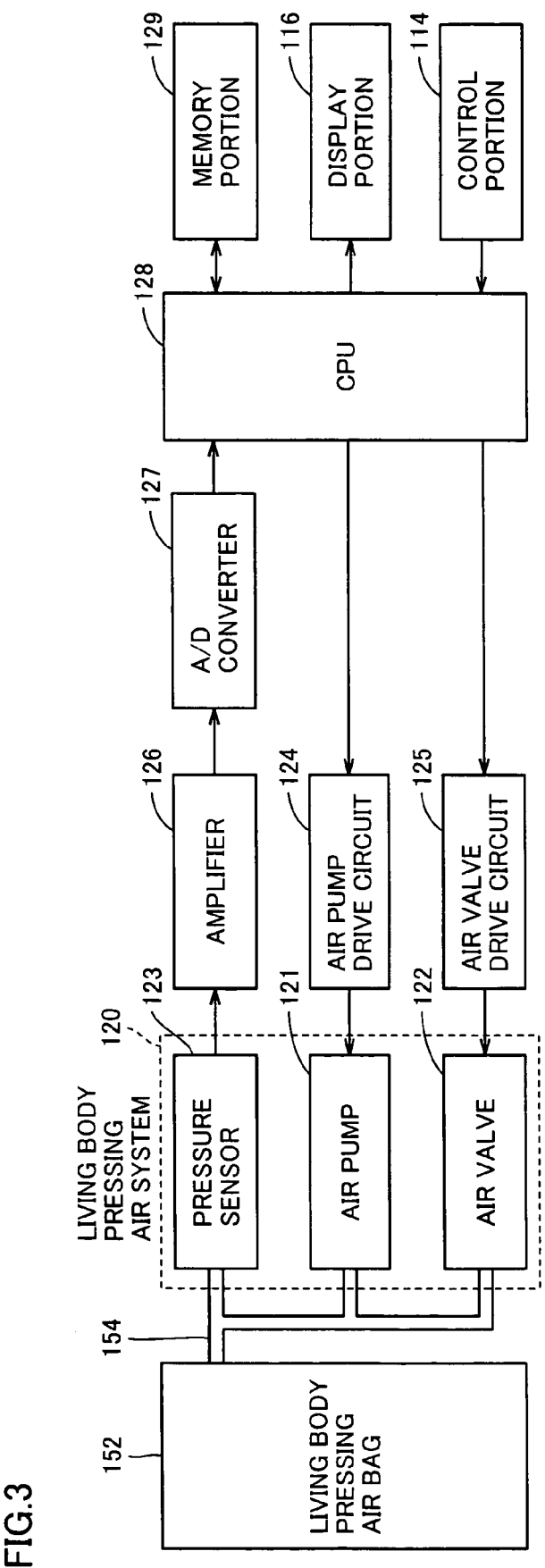
FIG. 3 is a functional block diagram of the blood pressure monitor of the first embodiment.

As shown in FIG. 3, a living body pressing air bag 152 included in the cuff is connected via an air tube 154 to a living body pressing air system 120. A CPU (central processing unit) 128 controls an operation of living body pressing air system 120.

Living body pressing air system 120 includes an air pump 121, an air valve 122, and a pressure sensor 123. Air pump 121 is provided for pressurizing a bladder of living body pressing air bag 152, which is driven by an air pump drive circuit 124 having received a command from CPU 128. Upon measurement, air pump 121 introduces compressed gas into the bladder of living body pressing air bag 152 to make it attain a prescribed pressure. Air valve 122 is provided for keeping or reducing the pressure in the bladder of living body pressing air bag 152, which is controlled to open and close by an air valve drive circuit 125 having received a command from CPU 128. Upon measurement, air valve 122 functions to keep and reduce the pressure of the bladder of living body pressing air bag 152 having attained a high-pressure state by air pump 121. After completion of the measurement, air valve 122 causes the bladder of living body pressing air bag 152 to return to the atmospheric pressure. Pressure sensor 123 is provided for detecting a pressure of the bladder of living body pressing air bag 152. Upon measurement, pressure sensor 123 detects the pressure of the bladder of living body pressing air bag 152 that changes from moment to moment, and outputs signals corresponding to the detected values to an amplifier 126. Amplifier 126 amplifies the signals output from pressure sensor 123 and outputs the amplified signals to an A/D converter 127. A/D converter 127 digitalizes the analog signals received from amplifier 126, and outputs the resultant signals to CPU 128.

CPU 128 controls living body pressing air system 120 based on commands input via control portion 114 provided at main unit 110 of blood pressure monitor 100A, and outputs a result of measurement to display portion 116 and a memory portion 129. Memory portion 129 is provided for storing the measurement results.

In blood pressure monitor 100A of the present embodiment, all the functional blocks shown in FIG. 3 except for living body pressing air bag 152 and pressure sensor 123 are provided at main unit 110, and accommodated in main unit casing 112. Living body pressing air bag 152 and pressure sensor 123 are provided at living body insert portion 140, and accommodated in living body insert portion casing 142. Living body pressing air bag 152, air pump 121 and air valve 122 are connected via a flexible air tube, and pressure sensor 123 and amplifier 126 are connected via a flexible signal line. The flexible air tube and the flexible signal line used to connect the components accommodated in main unit casing 112 and those accommodated in living body insert portion casing 142 can follow the pivotal movement of living body insert portion casing 142 to enable injection/discharge of the air and transmission/reception of the signals.

Hereinafter, the pivotal movement of the living body insert portion of the blood pressure monitor of the present embodiment as well as a more detailed configuration of the pivot connection mechanism will be described with reference to FIGS. 4-6.

As described above, in blood pressure monitor 100A of the present embodiment, main unit casing 112 and living body insert portion casing 142 are separated from each other, and the pivot connection mechanism including a pivot connects the separated main unit casing 112 and living body insert portion casing 142.

Figure 4:
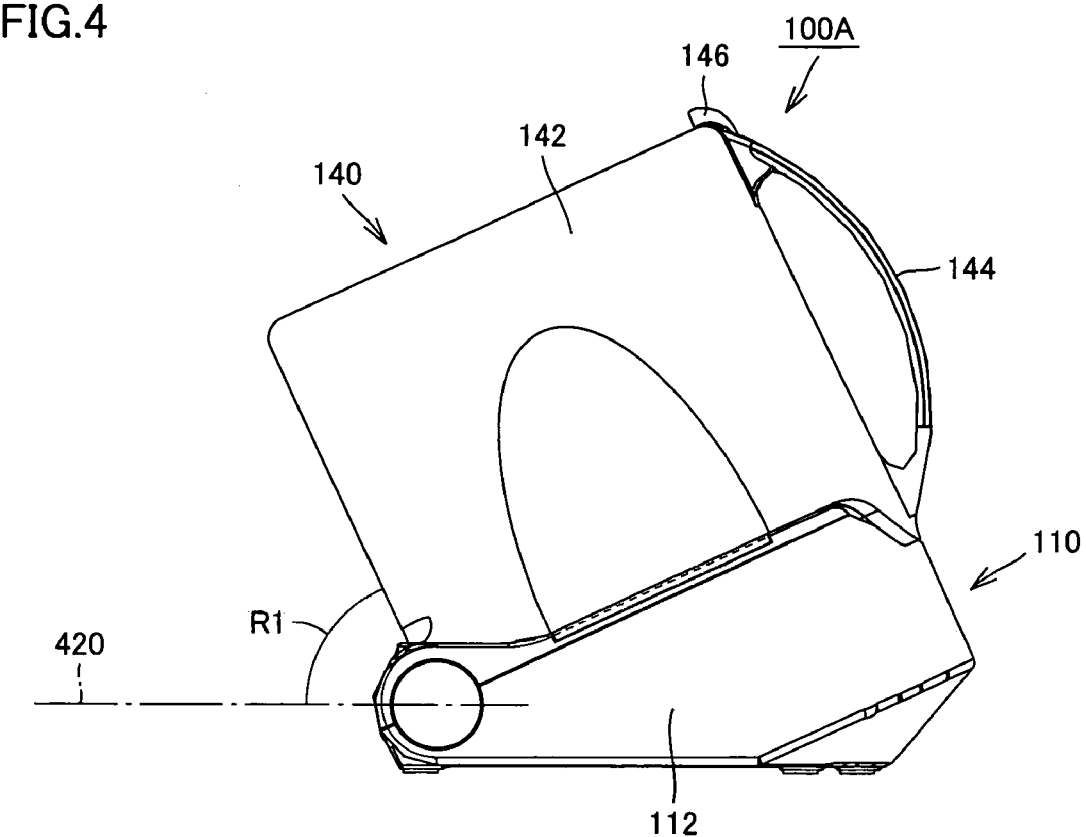
FIG. 4 is a right side view of the blood pressure monitor of the first embodiment, showing the non-use state where a casing of a living body insert portion is positioned on a casing of a main unit.

As shown in FIG. 4, when blood pressure monitor 100A is not in use (and left in place), living body insert portion casing 142 is rested on main unit casing 112. The upper surface of main unit casing 112 is formed slopewise in advance such that when it is placed on a horizontal table or the like, it is arranged at a prescribed angle with respect to the horizontal plane. Living body insert portion casing 142 is rested on main unit casing 112 in such a manner that the axis line of hollow opening 150 of living body insert portion casing 142 is orthogonal to the upper surface of main unit casing 112 thus inclined. Here, the inclination angle of living body insert portion casing 142 with respect to the horizontal plane in the non-use state is represented as R1.

The pivotal movement of living body insert portion casing 142 caused by a subject is restricted within a pivotally movable range. As shown in FIG. 5, when living body insert portion casing 142 attains a maximum moved state to the side of the subject within the movable range, living body insert portion casing 142 comes closer to the subject than main unit casing 112. In this state, the axis line of hollow opening 150 is tilted to the extent slightly beyond the state parallel to the horizontal plane. Here, the inclination angle of living body insert portion casing 142 with respect to the horizontal plane in the maximum moved state is represented as R2.

Figure 5:
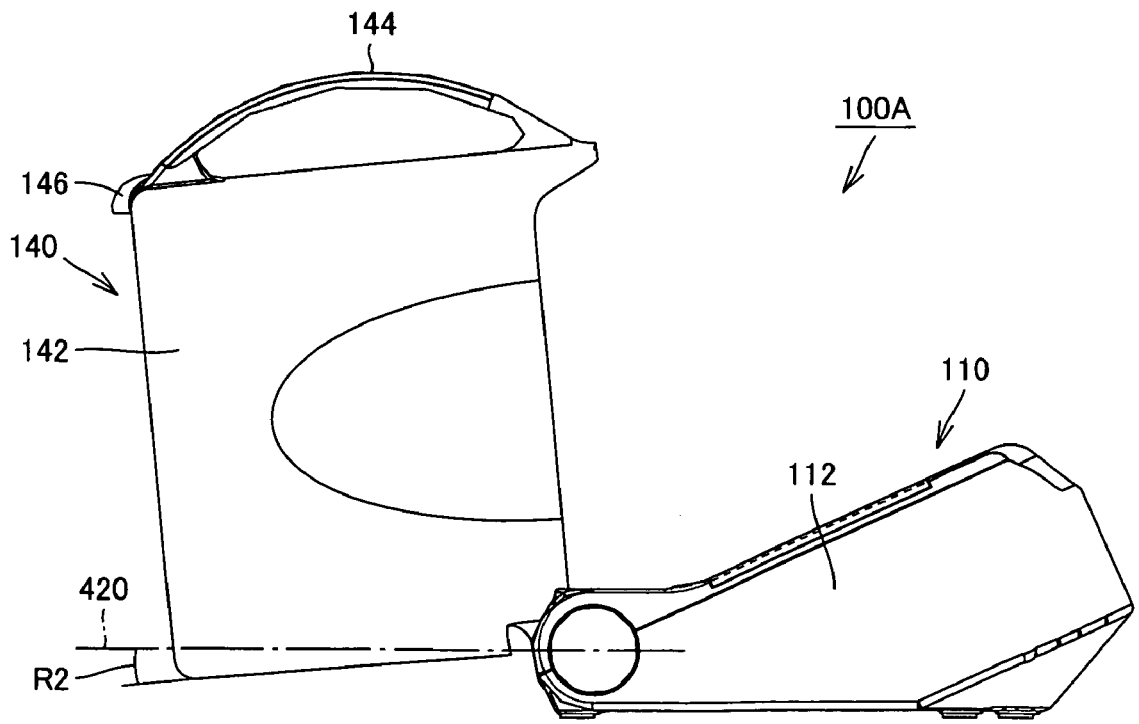
FIG. 5 is a right side view of the blood pressure monitor of the first embodiment, showing the maximum moved state where the living body insert portion casing is pivotally moved toward a subject as much as possible.

In blood pressure monitor 100A of the present embodiment, living body insert portion casing 142 can pivotally move freely, by an operation of the subject, within the movable range from the position corresponding to the non-use state shown in FIG. 4 to the position corresponding to the maximum moved state shown in FIG. 5. In other words, living body insert portion casing 142 pivotally moves from the position in the non-use state to approach the subject within the range of the angle (R1+R2).

In blood pressure monitor 100A of the present embodiment, it is preferable that torque required to be applied to the pivot to pivotally move living body insert portion casing 142 is smaller than torque that is imposed on the pivot during the measurement in accordance with the change in pressure of the cuff, or the torque that is applied to the pivot by living body insert portion casing 142 during the measurement when living body insert portion casing 142 is pressed by inflation or deflation of the cuff. When the torque of the pivot is adjusted in this manner, the movement of living body insert portion casing 142 in accordance with the change in pressure of the cuff during the measurement is no longer restricted. Thus, contact of the cuff with the living body improves, and blood pressure can be measured with high accuracy.

In blood pressure monitor 100A of the present embodiment, the pivot connection mechanism may also include a dumper or a friction spring for the purpose of suppressing abrupt pivotal movement of living body insert portion casing 142. The dumper or the friction spring may be provided at a connecting portion between the pivot and living body insert portion casing 142 or/and main unit casing 112. This configuration can suppress abrupt pivotal movement of living body insert portion casing 142 for example when the subject suddenly changes the posture during the measurement, so that occurrence of an artifact error due to detection of abnormal pressure pulse waves can be prevented. Further, operability for adjusting living body insert portion casing 142 to a desired angle when applying the cuff to the living body can be improved.

Figure 6:
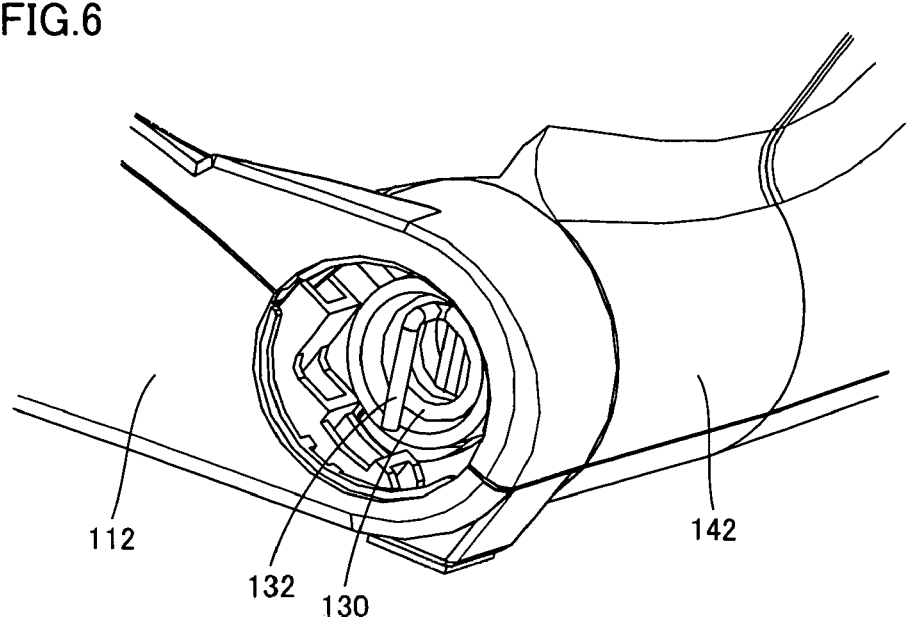
FIG. 6 is an enlarged view of a region VI shown in FIG. 2 of the blood pressure monitor of the first embodiment.

FIG. 6 shows an embodiment in the case where the above-described pivot connection mechanism is provided with the friction spring in the form of a coil spring. In FIG. 6, part of the main unit casing is not illustrated for ease of understanding of the shape of the coil spring.

As shown in FIG. 6, the pivot connection mechanism includes, in addition to the pivot, a coil spring 130 as the bias portion for biasing living body insert portion casing 142 in a direction away from main unit casing 112 in the non-use state. For example, coil spring 130 has an end secured to main unit casing 112, and another end 132 secured to living body insert portion casing 142. With this configuration, coil spring 130 suppresses abrupt pivotal movement of living body insert portion casing 142.

Hereinafter, a configuration and an operation of the unlocking/locking mechanism of the blood pressure monitor of the present embodiment will be described with reference to FIGS. 7-9.

Figure 7:
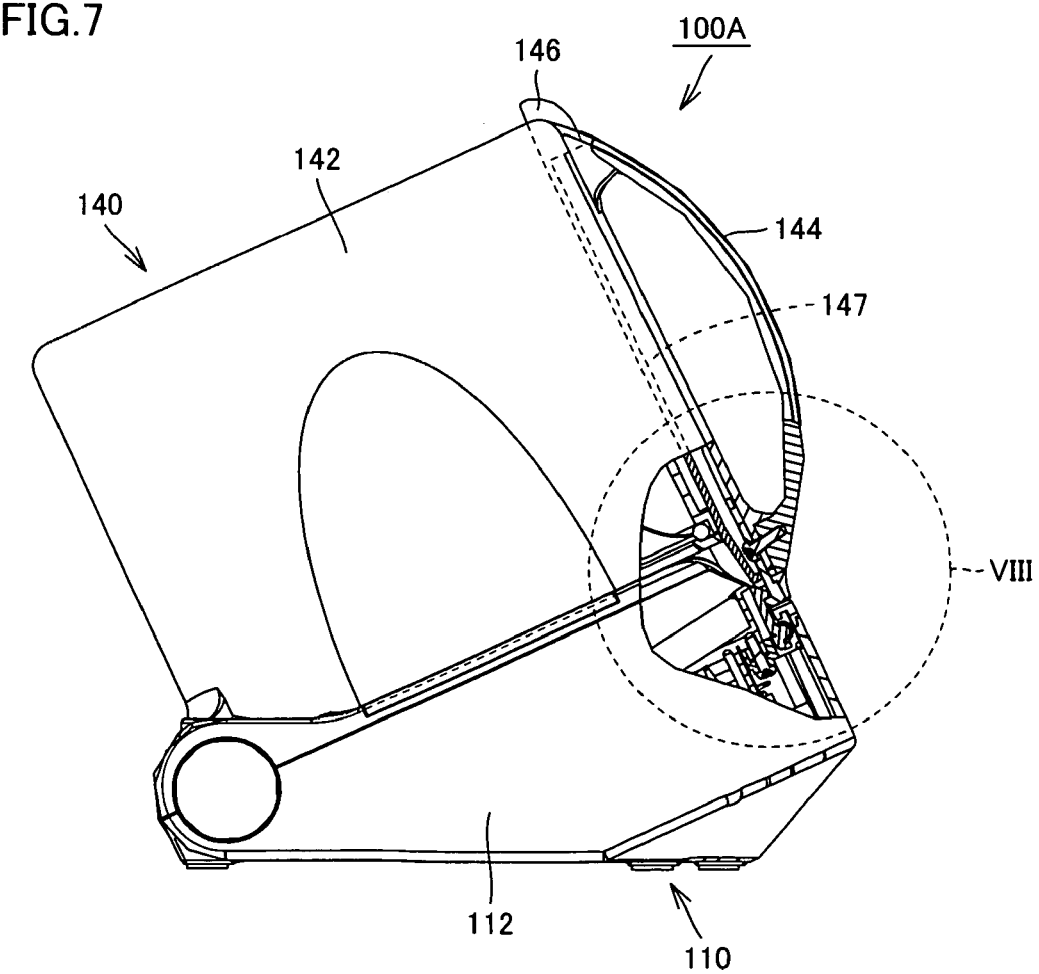
FIG. 7 is a partially cutaway side view illustrating an unlocking/locking mechanism of the blood pressure monitor of the first embodiment.

As shown in FIG. 7, living body insert portion casing 142 is rested on and secured to main unit casing 112 in the non-use state. That is, in the non-use state, living body insert portion casing 142 is secured to main unit casing 112 by the locking portion in opposition to the elastic bias force of coil spring 130 serving as the above-described bias portion. The locking portion is formed of a hook 117 provided at main unit casing 112 and another hook 143 provided at living body insert portion casing 142.

Figure 8A:
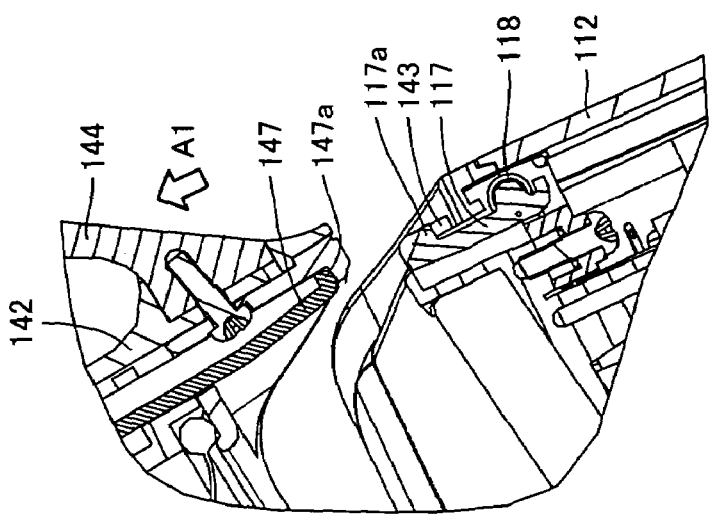
FIGS. 8A-8C are enlarged views of a region VIII shown in FIG. 7 of the blood pressure monitor of the first embodiment, showing an unlocking operation for releasing the lock of the living body insert portion with respect to the main unit so that the living body insert portion can move in a pivotable manner.

As shown in FIGS. 7 and 8A, an unlocking lever 147 cooperating with unlocking button 146 extends inside living body insert portion casing 142. An end 147a of unlocking lever 147 reaches main unit casing 112, and abuts hook 117 provided at main unit casing 112. An end 117a of hook 117 is engaged with hook 143 provided at living body insert portion casing 142, and coil spring 118 elastically biases hook 117 to maintain the engagement.

Figure 8B:
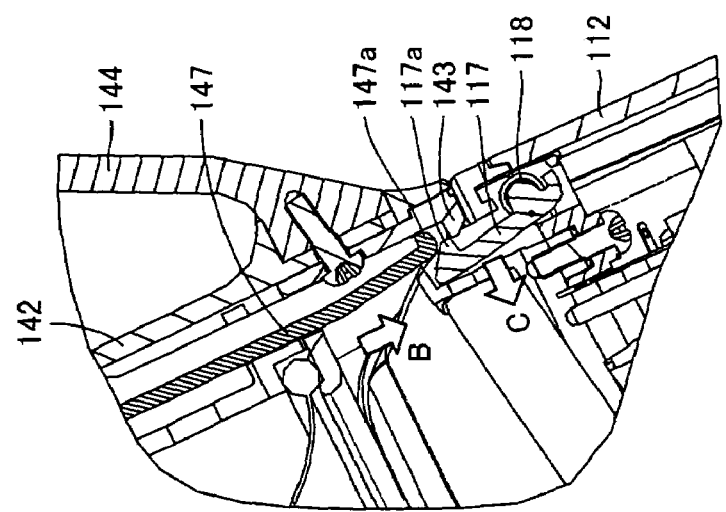
Figure 8C:
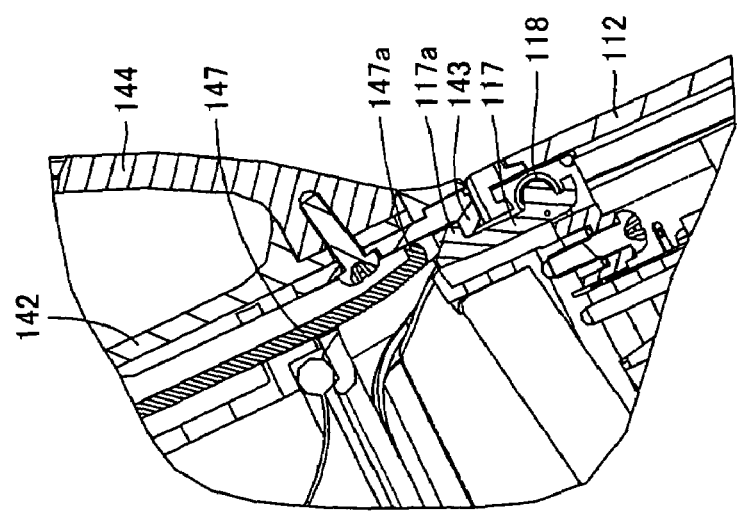

As shown in FIG. 8B, when unlocking button 146 is depressed, unlocking lever 147 moves in the direction shown by an arrow B in the figure, and end 147a of unlocking lever 147 presses downward a tapered surface provided at the upper end of hook 117. This causes hook 117 to rotate in the direction shown by an arrow C in the figure in opposition to the bias force of coil spring 118. With the rotation of hook 117, end 117a of hook 117 is disconnected from hook 143 of living body insert portion casing 142, as shown in FIG. 8C, and the lock of living body insert portion casing 142 with main unit casing 112 is released. This enables pivotal movement of living body insert portion casing 142 with respect to main unit casing 112.

Figure 9:
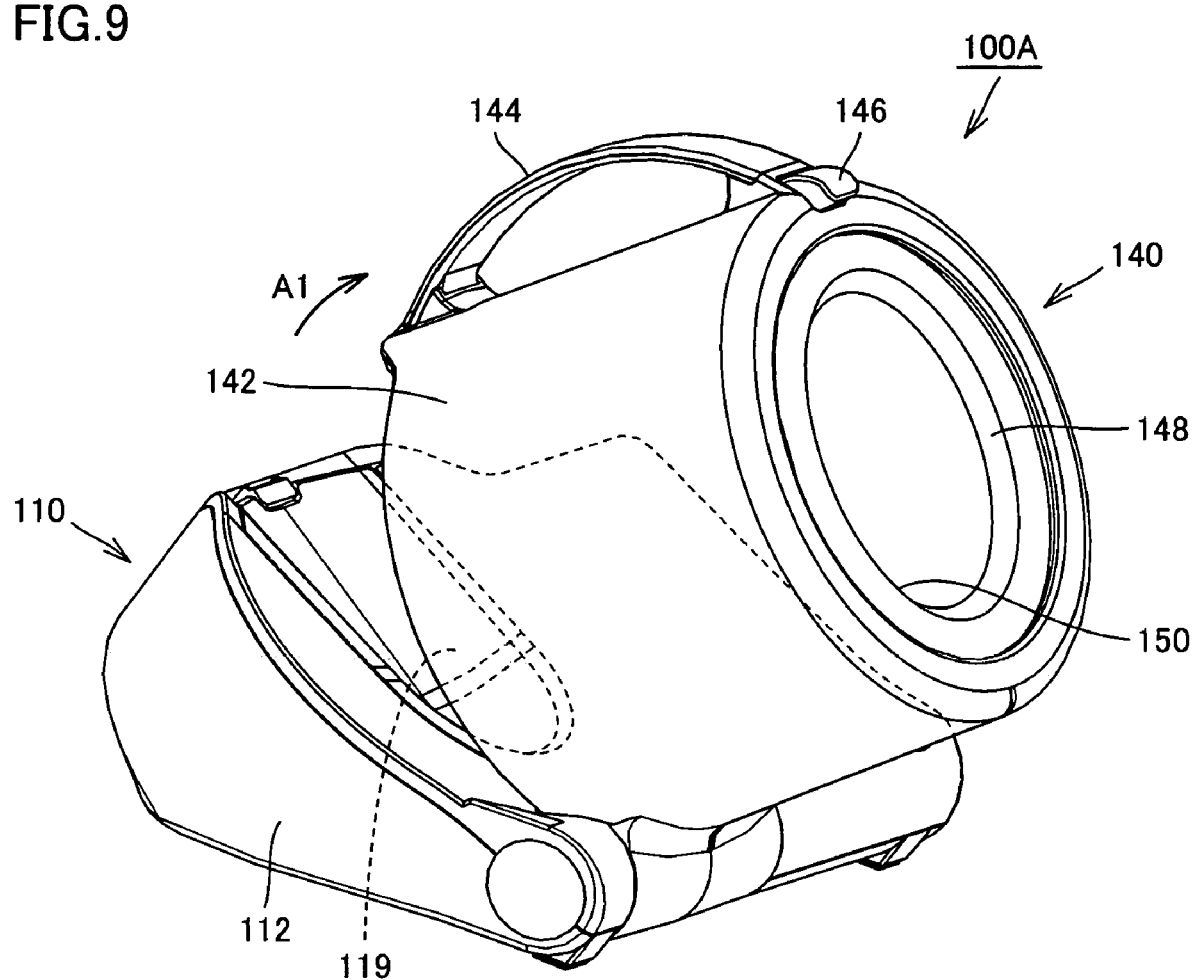
FIG. 9 is a perspective view of the blood pressure monitor of the first embodiment, showing the state where the lock is released.

Once the engagement is released, living body insert portion casing 142 is pressed upward by the bias force of the above-described coil spring 130 shown in FIG. 6 to the position shown in FIG. 9. Specifically, living body insert portion casing 142 pivotally moves about the pivot toward the subject to come closer to the subject than main unit casing 112, and stops at a position where its own weight balances with the elastic bias force of coil spring 130. It is noted that the position where living body insert portion casing 142 stops moving after the unlocking operation may be set to a desired angle by altering the elastic bias force of coil spring 130 as well as the own weight of living body insert portion casing 142 as appropriate.

Hereinafter, a procedure for applying the cuff and a measurement operation in the blood pressure monitor of the present embodiment will be described with reference to FIGS. 10 and 11. Although it is assumed that the right arm is used for measurement of a blood pressure value in FIGS. 10 and 11, it is of course possible to measure the blood pressure value with the left arm.

Figure 10:
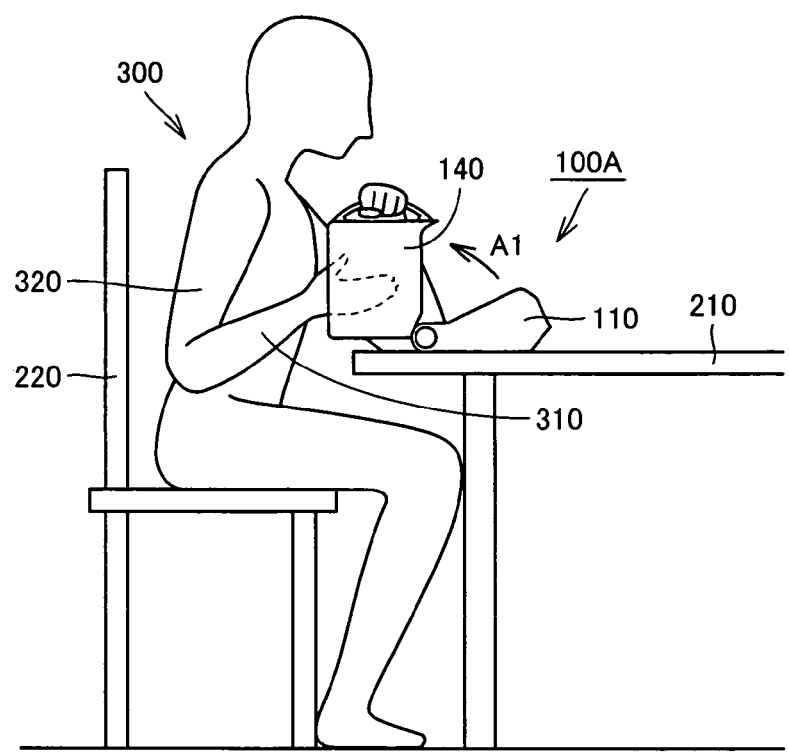
FIG. 10 is a schematic diagram illustrating a procedure for applying a cuff in the blood pressure monitor of the first embodiment, showing how an arm is inserted into a hollow opening of the living body insert portion.
Figure 11:
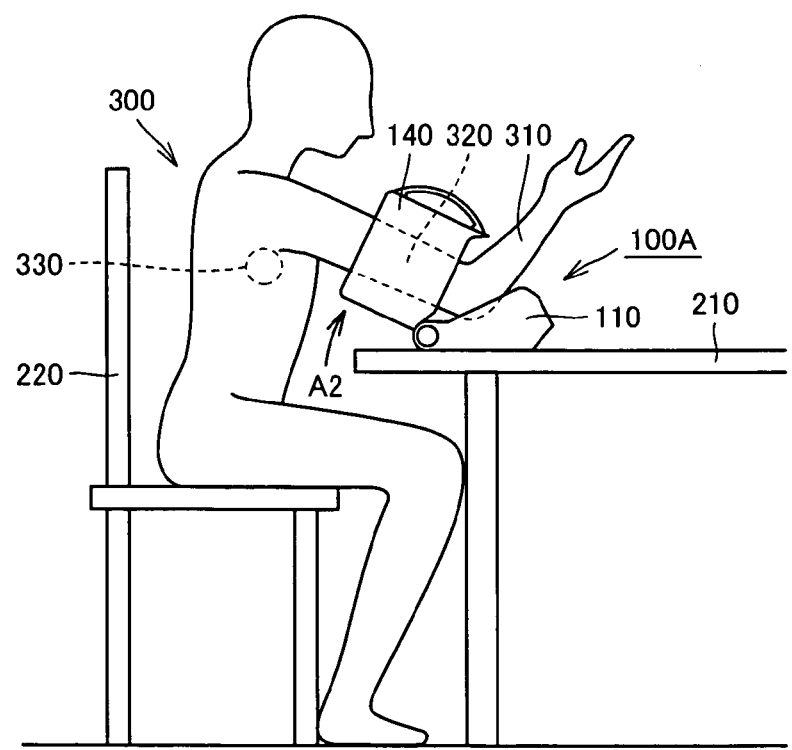
FIG. 11 is a schematic diagram illustrating a posture for measurement after application of the blood pressure monitor of the first embodiment.

As shown in FIG. 10, upon measurement of a blood pressure value with blood pressure monitor 10A of the present embodiment, main unit 110 of blood pressure monitor 100A is placed on a desk 210 having a horizontal surface, and a subject 300 sits on a chair 220. Depressing unlocking button 146, subject 300 moves living body insert portion 140 in the direction shown by an arrow A1 in the figure. Subject 300 then inserts the right hand into hollow opening 150 of living body insert portion 140, while gripping handle 144 provided at living body insert portion casing 142 of blood pressure monitor 100A with the left hand to adjust the inclination angle of living body insert portion 140. Subject 300 inserts the right hand to the further depth of hollow opening 150, until a forearm 310 and then an upper arm 320 faces the cuff provided in living body insert portion 140. With slightly bending the elbow of the right arm inserted in hollow opening 150, subject 300 rests the elbow on elbow rest 119 provided at the upper surface of main unit 110, to thereby take the posture for measurement as shown in FIG. 11.

During the procedure for applying the cuff, the inclination angle of living body insert portion 140 changes in accordance with the inclination angle of the right arm. Specifically, living body insert portion 140 turns following the movement of the right hand, as the right hand and then the right arm inserted in hollow opening 150 of living body insert portion 140 contact the inner peripheral surface of hollow opening 150. For example, at the stage where the right hand is inserted, it is preferable that living body insert portion 140 is turned in advance to the position corresponding to the maximum moved state as shown in FIG. 10 or closer thereto, to reduce the burden imposed on the subject. At the subsequent stage where the right hand and then the right arm is further inserted, however, it is preferable that living body insert portion 140 pivotally moves in the direction shown by an arrow A2 in the figure in accordance with the movement of the right hand and arm. In blood pressure monitor 100A of the present embodiment, the torque required to be applied to the pivot to rotate living body insert portion 140 is adjusted to allow living body insert portion 140 to follow the movement of the right hand and arm.

In the posture for measurement shown in FIG. 10, subject 300 stands erect, instead of slouching forward as in the conventional case. Thus, a heart 330 and upper arm 320 as the measurement site can be maintained at an approximately identical level in height, thereby enabling accurate measurement of the blood pressure value. This is uniquely because living body insert portion 140 pivotally moves frontward with respect to main unit 110. With the configuration of blood pressure monitor 100A as in the present embodiment, the subject is unnecessary to pull chair 220 closer to the desk or move blood pressure monitor 100A closer to the subject after inserting upper arm 320 into living body insert portion 140, and thus, usability of the blood pressure monitor considerably improves.

Figure 12:
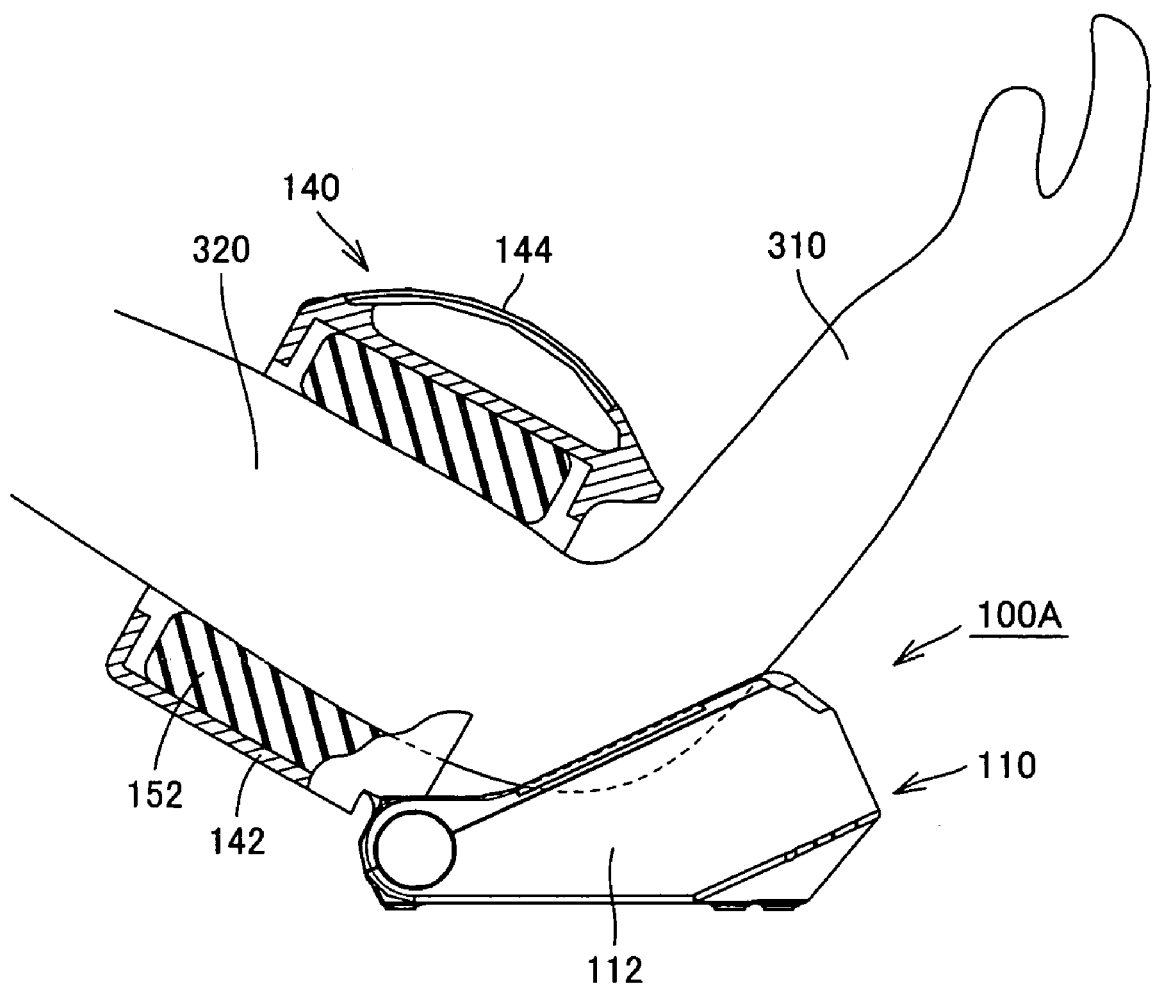
FIG. 12 is a schematic cross sectional view showing a posture for measurement of a blood pressure value using the blood pressure monitor of the first embodiment.

As shown in FIG. 12, in blood pressure monitor 100A of the present embodiment, arterial pressure pulse waves caused in the artery located within upper arm 320 by inflation/deflation of living body pressing air bag 152 are detected to measure the blood pressure value. During the measurement as well, living body insert portion 140 rotates following the movement of the upper arm. This ensures good contact between the cuff and the living body, and measurement with high accuracy becomes possible.

When the above-described configuration of the blood pressure monitor of the present embodiment is employed, the subject can take an unconstrained posture during the measurement under any conditions, without suffering unnecessary pain. As a result, it is possible to stably and accurately measure the blood pressure value.

Second Embodiment

A blood pressure monitor according to the present embodiment is identical to that of the first embodiment in that it detects arterial pressure pulse waves by pressing an upper arm of a subject to measure a blood pressure value and also in that the cuff is wound around the upper arm automatically by an automatic cuff winding mechanism. Thus, the portions similar to those of the blood pressure monitor of the first embodiment are denoted by the same reference characters, and description thereof will not be repeated here.

In the blood pressure monitor of the present embodiment, the living body insert portion casing and the main unit casing are connected to each other by a pivot connection mechanism including a pivot, as in the blood pressure monitor of the first embodiment. The living body insert portion casing moves with respect to the main unit casing in a pivotable manner, for which a wide movable range is ensured such that the subject can readily insert the arm to apply the cuff, again as in the blood pressure monitor of the first embodiment.

With the blood pressure monitor configured as described above, however, there may occur a case where a blood pressure value can be measured without hindrance even if the posture of the subject is not suitable for the measurement. Such a risk increases as the movable range of the living body insert portion casing is set wider. Accuracy in measurement may be degraded if there is a considerable difference in height between the upper arm around which the cuff is wound and the heart. In view of the foregoing, in the blood pressure monitor of the present embodiment, the inclination level detecting portion for detecting an inclination level of the living body insert portion casing is provided to solve such a problem. Here, the inclination level of the living body insert portion casing refers to the degree of inclination of the living body insert portion casing, which may be derived from the inclination angle with respect to the horizontal plane, the inclination angle with respect to the main unit casing, or an amount of movement of the living body insert portion casing with respect to the main unit casing.

Figure 13:
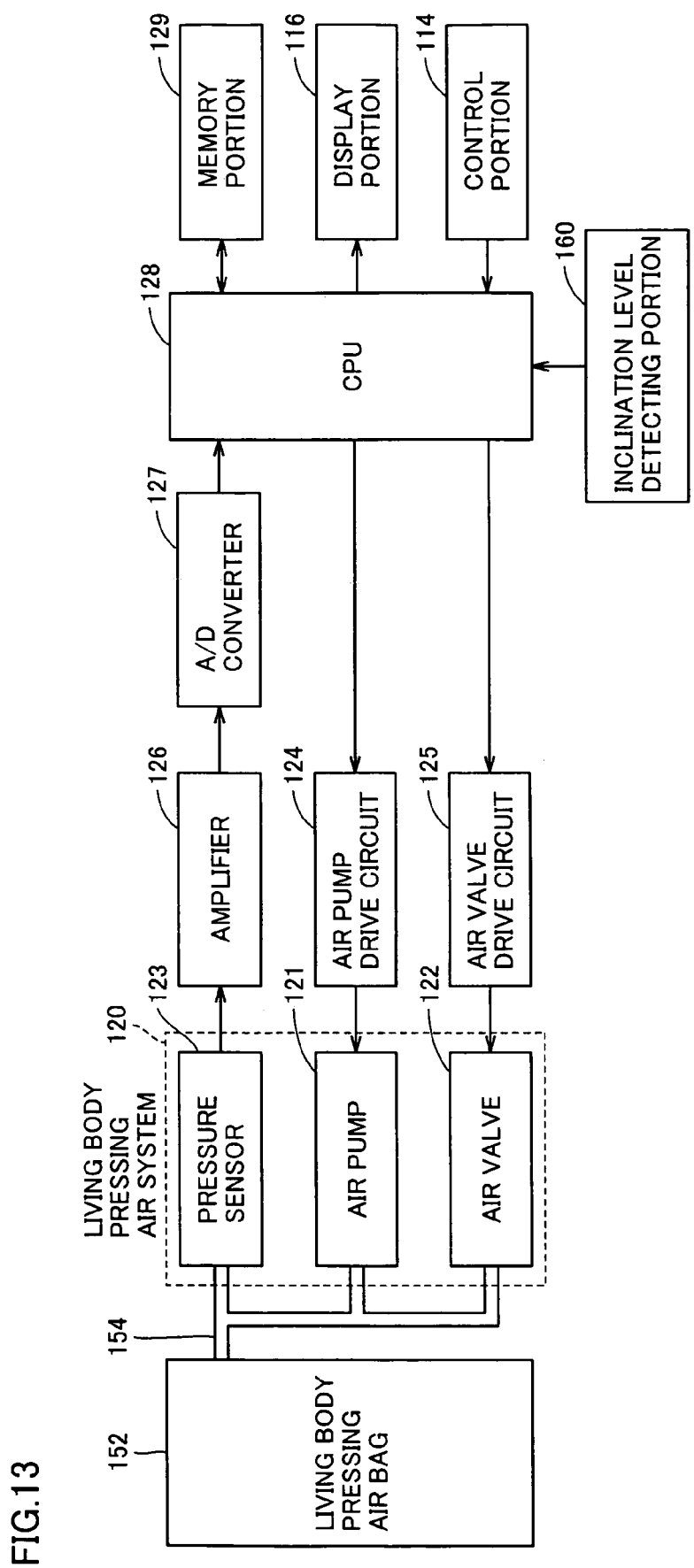
FIG. 13 is a functional block diagram of a blood pressure monitor according to a second embodiment of the present invention.

As shown in FIG. 13, the blood pressure monitor 100B of the present embodiment is provided with an inclination level detecting portion 160, and information about the inclination level of living body insert portion casing 142 detected by inclination level detecting portion 160 is output to CPU 128.

To realize the posture for measurement that keeps the difference between the height of the upper arm around which the cuff is wound and the height of the heart within a small range, an optimal range for the inclination angle of the upper arm inserted into hollow opening 150 of living body insert portion 140 is necessarily derived. The optimal range for the inclination angle of the upper arm corresponds to the inclination level of living body insert portion casing 142 at the time of measurement, and as a result, an optimal measurement range of living body insert portion casing 142 is decided.

Figure 14:
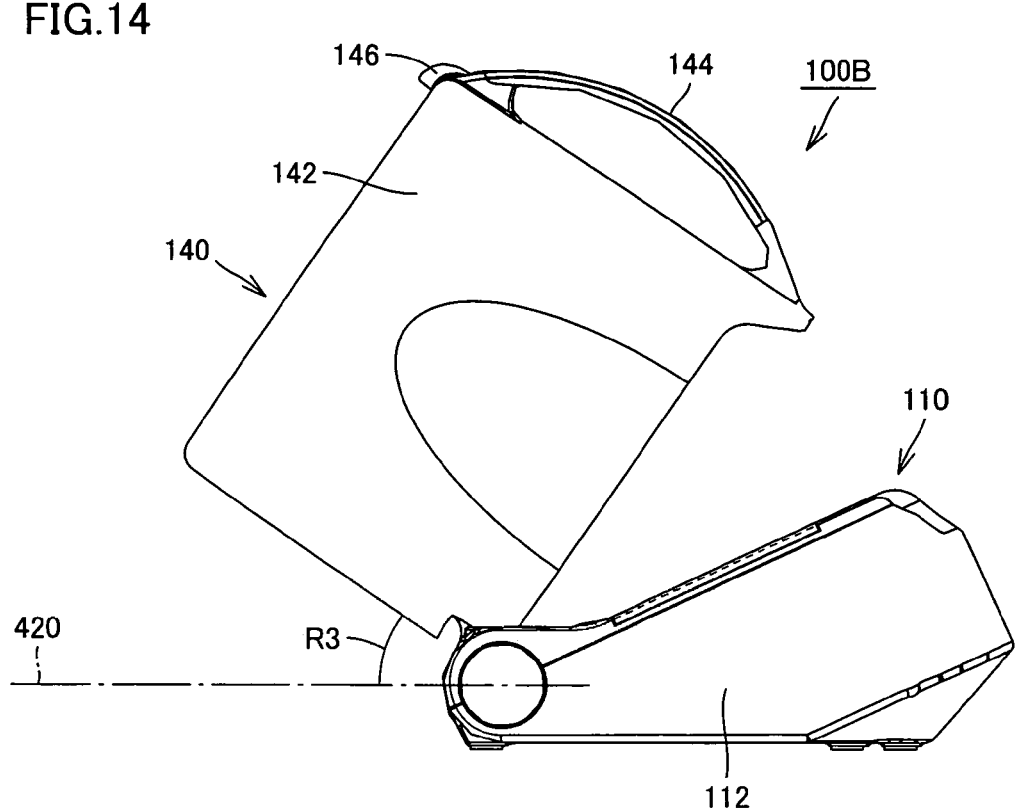
FIG. 14 is a right side view of the blood pressure monitor of the second embodiment, showing the state where the living body insert portion casing is positioned at a minimum moved position within an optimal measurement range.

FIG. 14 shows the state where the living body insert portion casing is in a minimum moved position within the optimal measurement range enabling accurate measurement of the blood pressure value. Here, the inclination angle of living body insert portion casing 142 with respect to the horizontal plane in this state is represented as R3.

Figure 15:
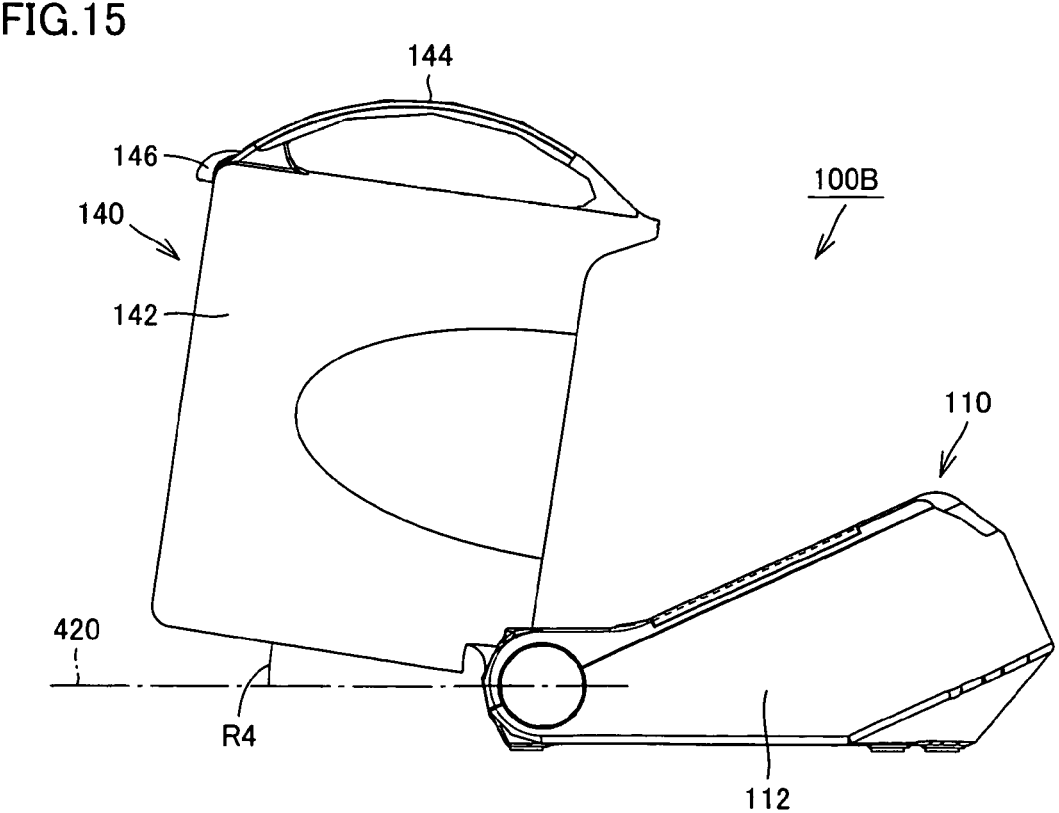
FIG. 15 is a right side view of the blood pressure monitor of the second embodiment, showing the state where the living body insert portion casing is positioned at a maximum moved position within the optimal measurement range.

FIG. 15 shows the state where the living body insert portion casing is in a maximum moved position within the optimal measurement range enabling accurate measurement of the blood pressure value. Here, the inclination angle of living body insert portion casing 142 with respect to the horizontal plane in this state is represented as R4.

Figure 16:
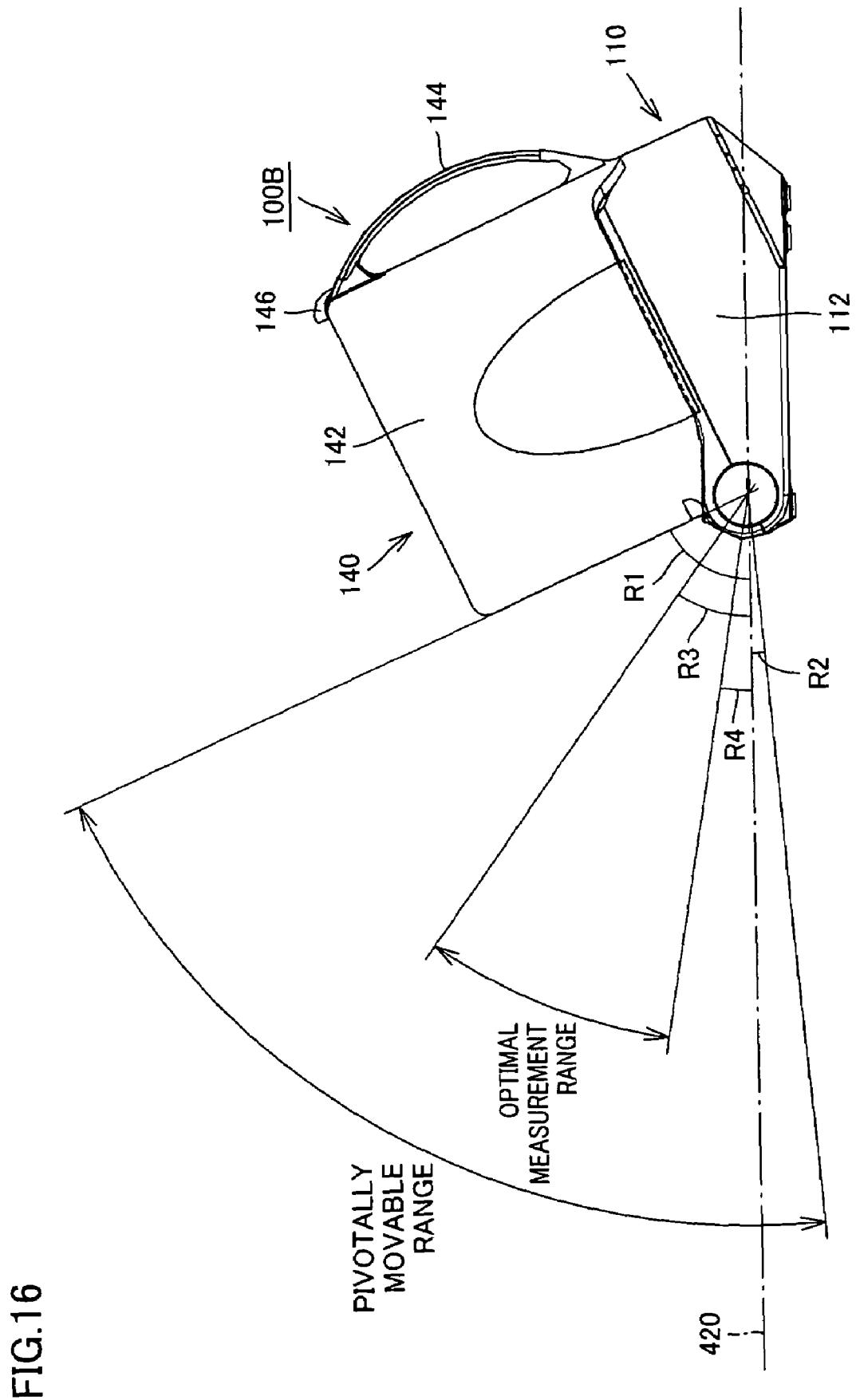
FIG. 16 shows the relation between a pivotally movable range and the optimal measurement range of the blood pressure monitor of the second embodiment.

As shown in FIG. 16, in blood pressure monitor 100B of the present embodiment, living body insert portion casing 142 freely turns within a movable range that is defined by inclination angles R1 and R2 shown in the figure. On the other hand, the optimal measurement range of living body insert portion casing 142 corresponds to the range from inclination angle R3 to inclination angle R4 shown in the figure. The optimal measurement range is included in the movable range, and has the inclination angle with respect to the horizontal plane preferably within the range from 15° to 45°.

As the inclination level detecting portion for detecting whether living body insert portion casing 142 is within the optimal measurement range or not, application of various sensors is conceivable. For example, as the means for directly detecting the inclination angle of living body insert portion casing 142 with respect to the horizontal plane or its inclination angle with respect to main unit casing 112, an angle sensor or the like may be employed. Further, as the means for indirectly detecting the inclination angle of living body insert portion casing 142 from the amount of movement of living body insert portion casing 142, a range sensor as typified by a photoelectric sensor (proximity sensor), a photoelectric sensor employing an encoder system, and the like may be employed. Furthermore, the inclination level may be detected using various switches. A tact switch, a rotary switch, a switch employing variable resistance, and the like may be used to detect the inclination angle of living body insert portion casing 142 indirectly from the amount of movement of living body insert portion casing 142.

Hereinafter, a way of detecting the inclination level of living body insert portion casing 142 using a tact switch will be described by way of example.

Figure 17:
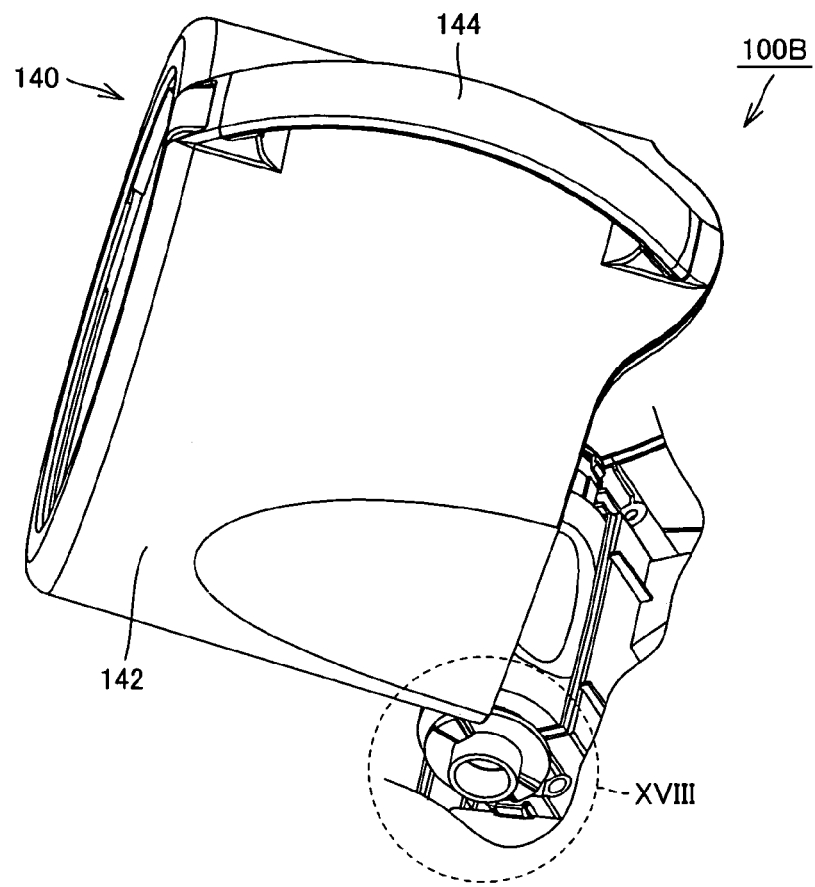
FIG. 17 is a partially cutaway perspective view of the blood pressure monitor of the second embodiment.
Figure 18:
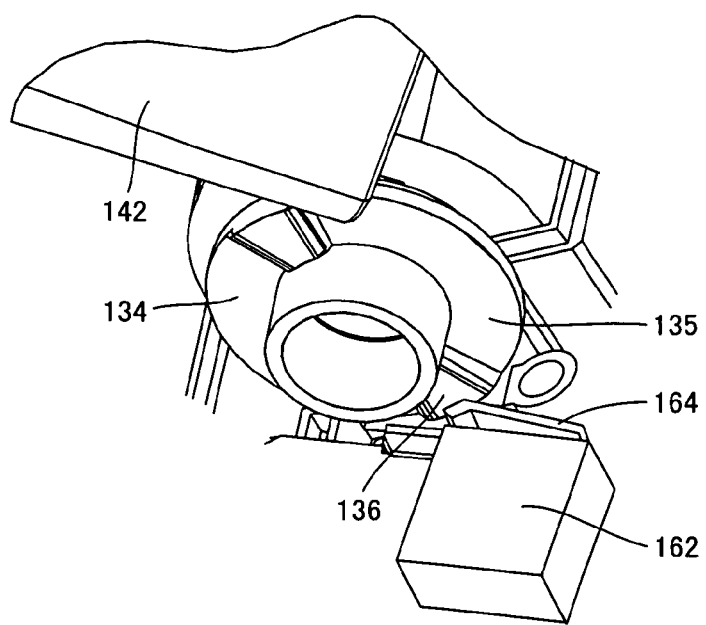
FIG. 18 is an enlarged view of a region XVIII shown in FIG. 17 of the blood pressure monitor of the second embodiment.

As shown in FIGS. 17 and 18, in blood pressure monitor 100B of the present embodiment, a rotary plate 134 is attached to an end of the pivot connecting living body insert portion casing 142 and main unit casing 112. Rotary plate 134 turns corresponding to the turn of living body insert portion casing 142. Provided on the surface of rotary plate 134 is a projection 136, which differs in height from another area 135 of the surface. A tact switch 162 serving as the inclination level detecting portion is arranged in the vicinity of rotary plate 134. A switch level 164 of tact switch 162 abuts the main surface of rotary plate 134 on which projection 136 is provided.

Projection 136 of rotary plate 134 is formed to have a predetermined width in angle in the circumferential direction. Specifically, it is formed to have the angle width the same as the angle defining the optimal measurement range of living body insert portion casing 142 described above. Switch lever 164, facing the main surface of rotary plate 134 provided with projection 136, causes tact switch 162 to attain an on state when it abuts projection 136, and to attain an off state when it abuts other area 135 not provided with projection 136.

With this configuration, tact switch 162 attains the on state when living body insert portion casing 142 is located within the optimal measurement range, whereas it attains the off state when living body insert portion casing 152 is located out of the optimal measurement range. By detecting the on/off state of the tact switch, it is possible to determine whether living body insert portion casing 142 is within the optimal measurement range or not. A result of the determination may be used, e.g., for an informing system that informs the subject as to whether the posture for measurement is acceptable or not. Hereinafter, a control flow for implementing such an informing system will be described.

Figure 19:
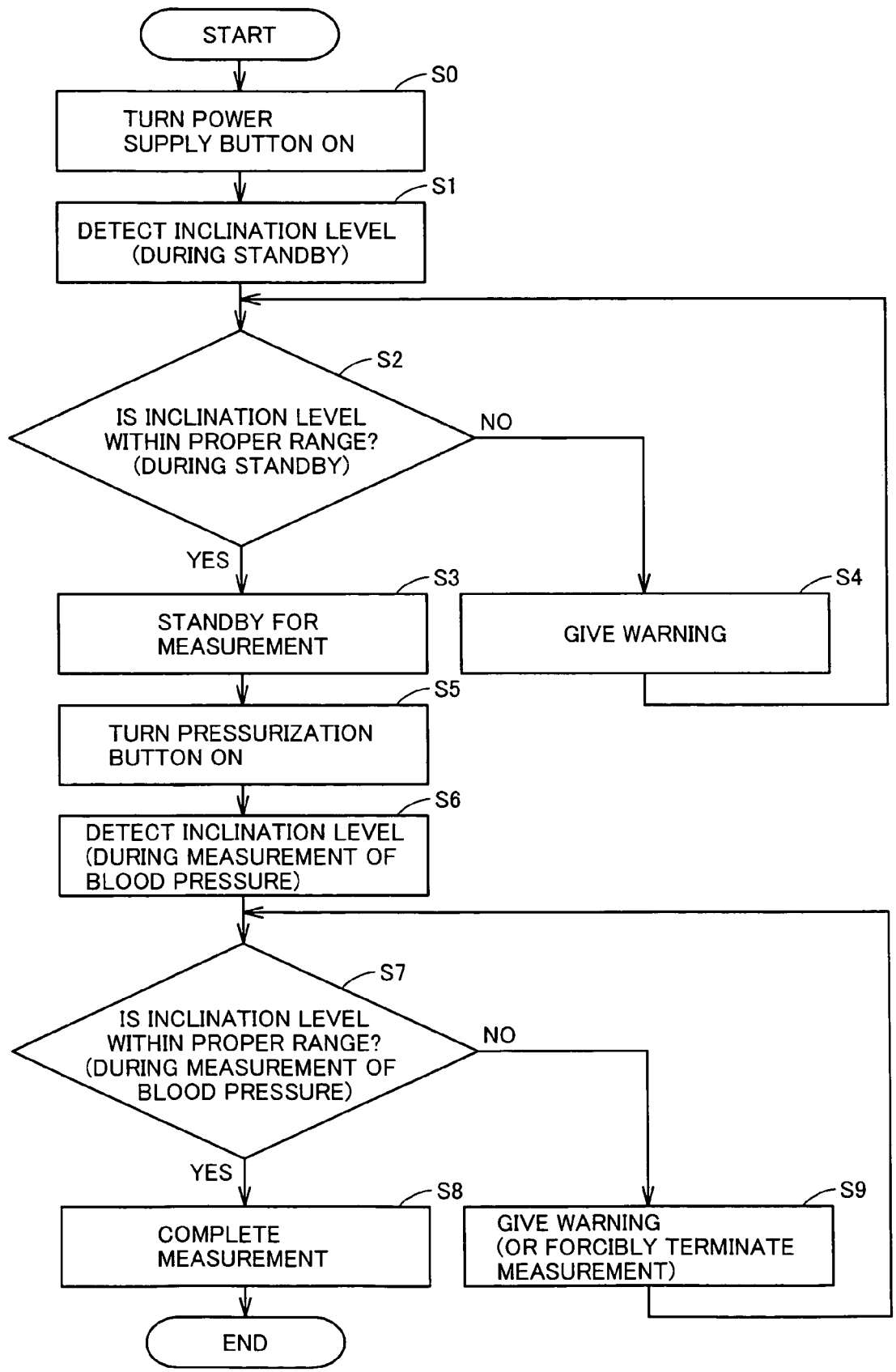
FIG. 19 shows a control flow of the blood pressure monitor of the second embodiment.

As shown in FIG. 19, in step S0, the power supply button is turned on to make blood pressure monitor 100B enter a standby state. In this standby state, the inclination level of living body insert portion casing 142 is detected (step S1). The inclination level of living body insert portion casing 142 detected in step S1 is output to CPU 128, and, in step S2, it is determined whether it is within the optimal measurement range. If the inclination level of living body insert portion casing 142 is within the optimal measurement range, the process goes to step S3 where blood pressure monitor 100B enters a standby state for measurement. If it is out of the optimal measurement range, warning is given to the subject in step S4. The way of giving warning will be described later.

Blood pressure monitor 100B having entered the measurement standby state in step S3 proceeds to the step (step S6) of detecting the inclination level of living body insert portion casing 142 again when the subject turns on a pressurization button (step S5). During this time, the inflating and deflating operations of the cuff are carried out, and detection of the arterial pressure pulse waves by the pressure sensor is conducted concurrently. In step S7, if it is determined that the inclination level of living body insert portion casing 142 is within the optimal measurement range, the process goes to step S8, where the measurement is finished. If it is determined that the inclination level of living body insert portion casing 142 is out of the optimal measurement range in step S7, the process goes to step S9, where warning is given to the subject or the measurement operation is forcibly terminated.

To give warning to the subject, various methods may be employed. For example, a warning display may be provided on the display portion, a warning sound may be emitted by a buzzer or the like, an LED (light-emitting diode) provided at the main unit or the living body insert portion of the blood pressure monitor may be turned on, or the blood pressure monitor itself may be made to vibrate. Hereinafter, a configuration of the display portion in the case where a liquid crystal display is used to display a warning to attract attention of the subject will be described.

Figure 20A:
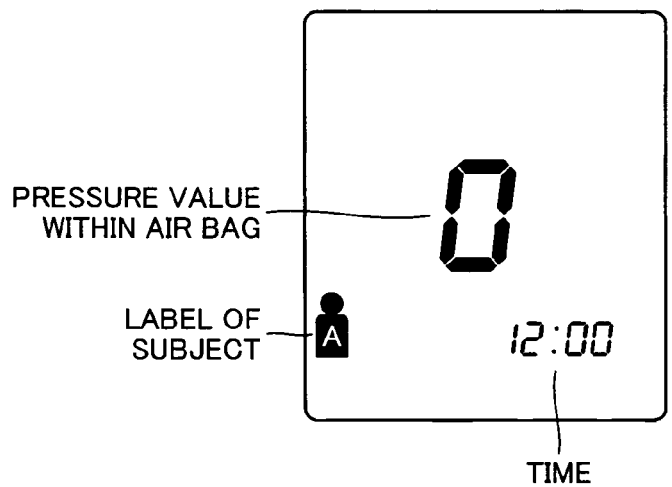
FIGS. 20A and 20B show a display example of a display screen in the blood pressure monitor of the second embodiment, FIG. 20A showing a display example when the inclination level of the living body insert portion casing during standby is within an optimal measurement range, while FIG. 20B showing a display example when the inclination level is out of the optimal measurement range and a warning to the subject is displayed.
Figure 20B:
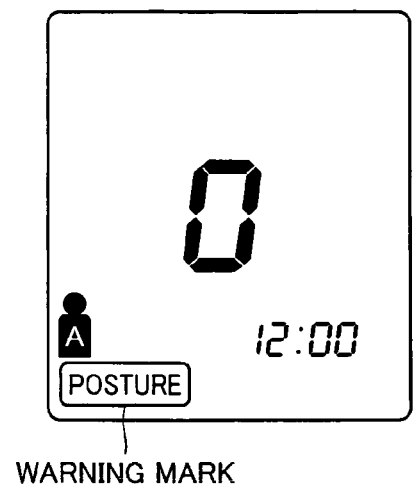

As shown in FIG. 20A, in the measurement standby state, display portion 116 displays a value indicating the pressure within the living body pressing air bag, a label of the subject, and time. In this state, if it is determined that the inclination level of living body insert portion casing 142 is out of the optimal measurement range, a warning mark is displayed on a prescribed position of display portion 116, as shown in FIG. 20B.

Figure 21A:
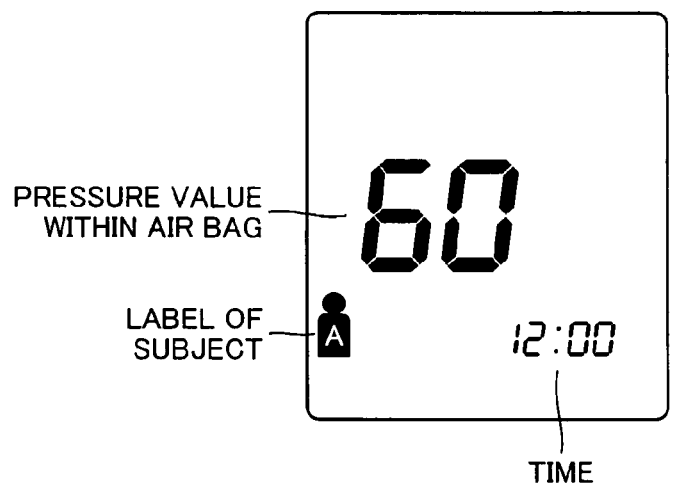
FIGS. 21A and 21B show another display example of the display screen in the blood pressure monitor of the second embodiment, FIG. 21A showing a display example when the inclination level of the living body insert portion casing during measurement is within the optimal measurement range, while FIG. 21B showing a display example when the inclination level is out of the optimal measurement range and a warning to the subject is displayed.
Figure 21B:
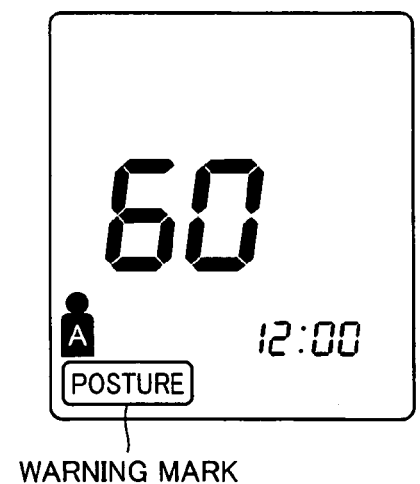

As shown in FIG. 21A, during the measurement operation, display portion 116 displays a pressure within the living body pressing air bag, a label of the subject, and time. In this state, if it is determined that the inclination level of living body insert portion casing 142 is out of the optimal measurement range, a warning mark is displayed on a prescribed position of display portion 116, as shown in FIG. 21B.

Figure 22A:
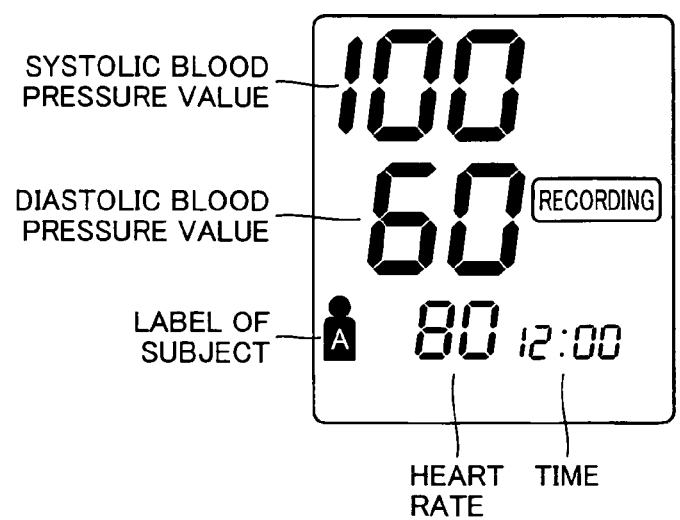
FIGS. 22A and 22B show yet another display example of the display screen in the blood pressure monitor of the second embodiment, FIG. 22A showing a display example of measurement results in the past that have been retrieved and displayed when the inclination level of the living body insert portion casing during measurement is within the optimal measurement range, while FIG. 22B showing a display example of the measurement results in the past having been retrieved and displayed when the inclination level is out of the optimal measurement range.
Figure 22B:
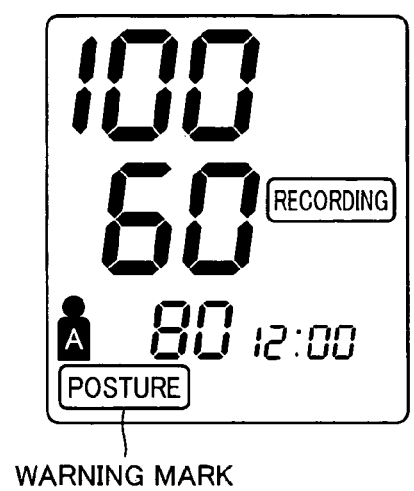

As shown in FIG. 22A, when the measurement data in the past are read out, display portion 116 displays the systolic blood pressure value and the diatolic blood pressure value measured in the past, a label of the subject, a heart rate, and time. When the data in the past have been retrieved, if the inclination level of living body insert portion casing 142 is out of the optimal measurement range, a warning mark is displayed on a prescribed position of display portion 116, as shown in FIG. 22B.

As described above, according to the blood pressure monitor of the present embodiment, determination is made as to whether the inclination level of the living body insert portion casing falls within a predetermined range in its movable range, and the result is informed to the subject, or the measurement is forcibly terminated, to control the blood pressure monitor not to proceed to the measurement operation when the inclination level of the living body insert portion casing is out of the predetermined range. With this configuration, it is possible to inform the subject as to whether the result of measurement is one obtained with accuracy or not, or to forcibly terminate the measurement when the conditions ensuring accurate measurement of the blood pressure value are not met. As a result, an adverse effect caused by ensuring a wide movable range of the living body insert portion casing can be prevented, and the intended purpose to make it possible to accurately measure the blood pressure value with an unforced posture is accomplished.

Third Embodiment

Hereinafter, a configuration of the blood pressure monitor according to the third embodiment of the present invention and a posture for measurement when using the relevant blood pressure monitor will be described. The portions similar to those of blood pressure monitor 100A of the first embodiment are denoted by the same reference characters, and description thereof is not repeated here.

Figure 23A:
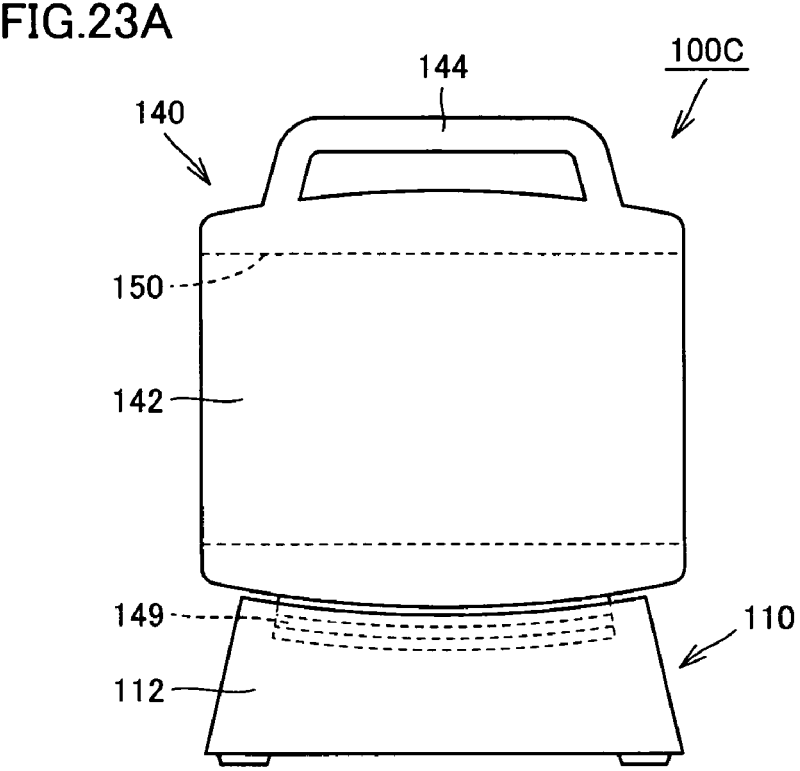
FIGS. 23A and 23B are side views of a blood pressure monitor according to a third embodiment of the present invention, in the non-use state and in the use state, respectively.

As shown in FIG. 23A, in the blood pressure monitor 100C of the present embodiment, main unit casing 112 and living body insert portion casing 142 are slidably connected by a slide connection mechanism. More specifically, the slide connection mechanism is formed, e.g., of a ridge 149 provided at the lower end of living body insert portion casing 142 with a prescribed radius of curvature, and a guide groove provided at the upper end of main unit casing 112 with a prescribed radius of curvature. Engagement of ridge 149 with the guide groove realizes the connection between living body insert portion casing 142 and main unit casing 112 in a slidable manner.

Figure 23B:
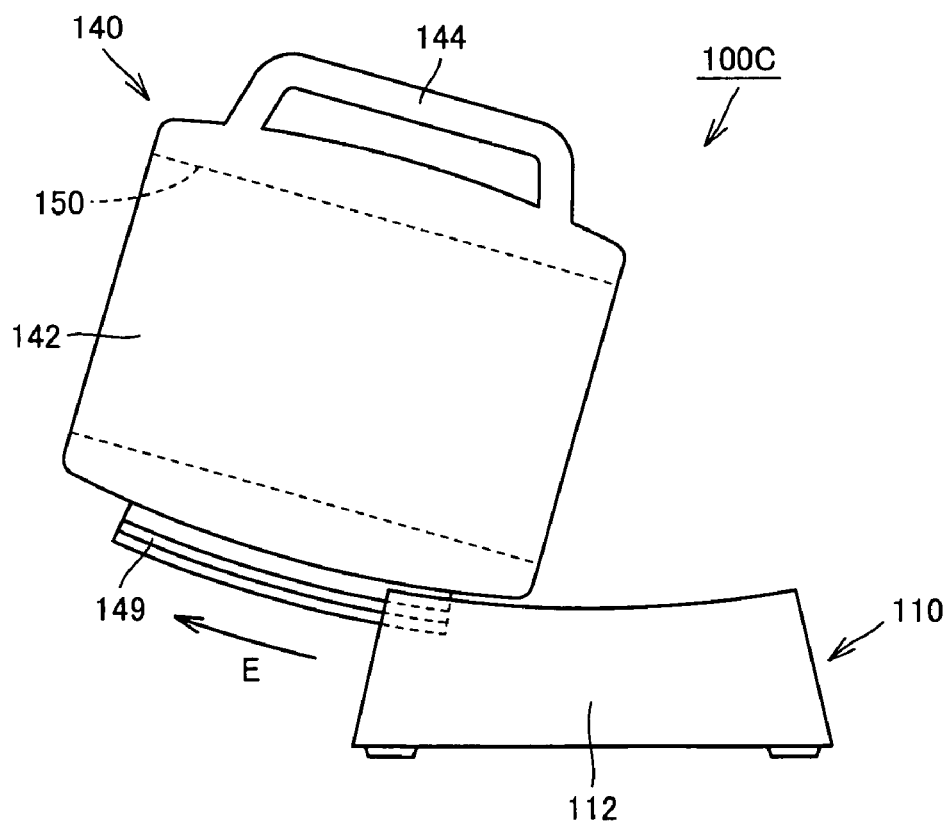

Upon application of the cuff to the upper arm, as shown in FIG. 23B, living body insert portion casing 142 moves toward the subject (in the direction shown by an arrow E in the figure) with respect to main unit casing 112. In blood pressure monitor 100C of the present embodiment, ridge 149 and the guide groove are both provided with a prescribed radius of curvature, so that living body insert portion casing 142 is inclined as it moves.

Figure 24:
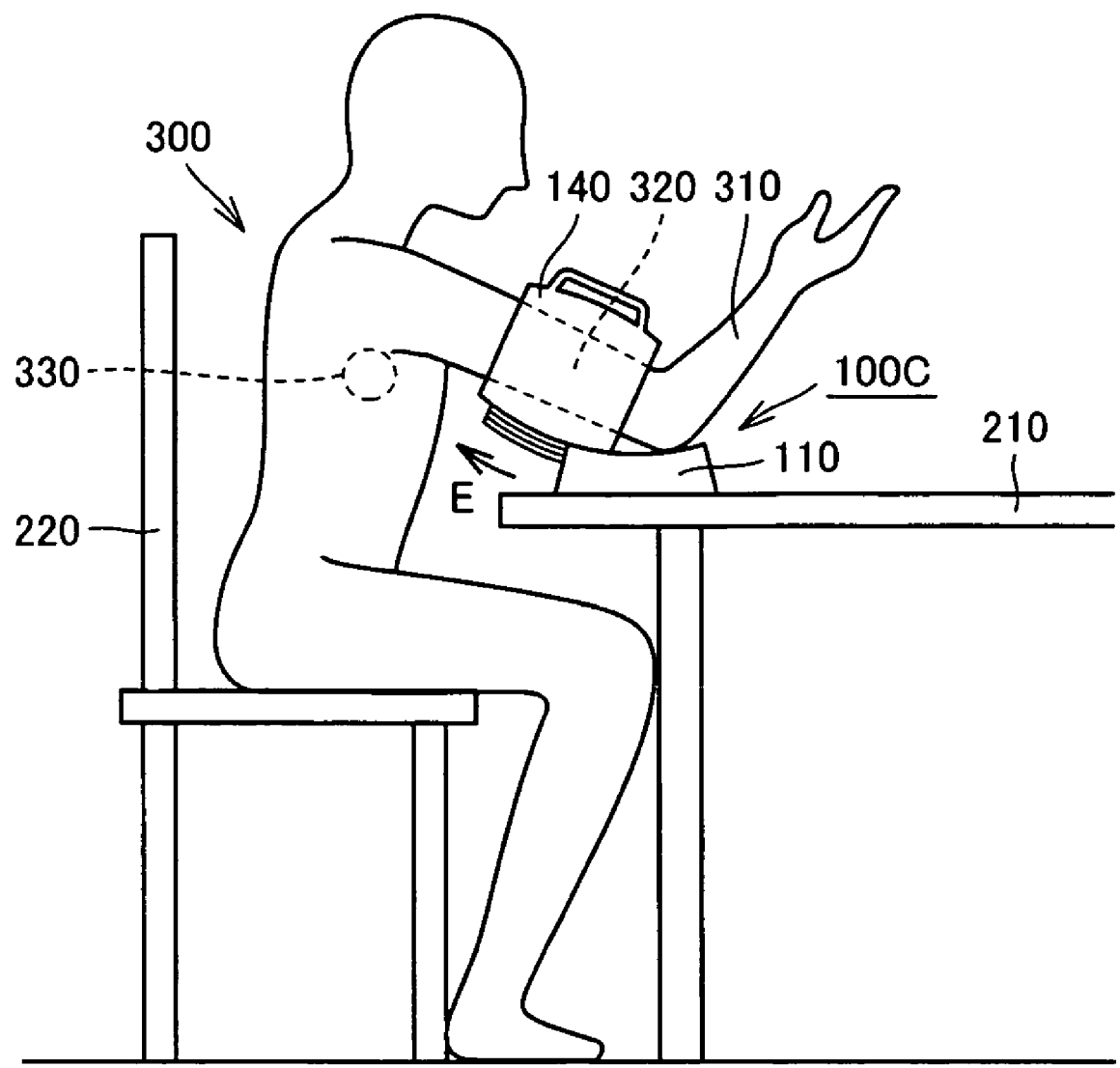
FIG. 24 is a schematic diagram illustrating a posture for measurement when using the blood pressure monitor of the third embodiment.

With this configuration, the posture for measurement as shown in FIG. 24 is realized, and similar effects to those of the first embodiment described above can be obtained. As a result, the subject does not need to suffer unnecessary pain during the measurement, and the measurement can be carried out with an unconstrained posture under any conditions. Accordingly, accurate and stable measurement of the blood pressure value becomes possible.

Fourth Embodiment

Hereinafter, a configuration of the blood pressure monitor of the fourth embodiment of the present invention and a posture for measurement when using the relevant blood pressure monitor will be described. The portions similar to those of blood pressure monitor 100A of the first embodiment are denoted by the same reference characters, and description thereof is not repeated here.

Figure 25A:
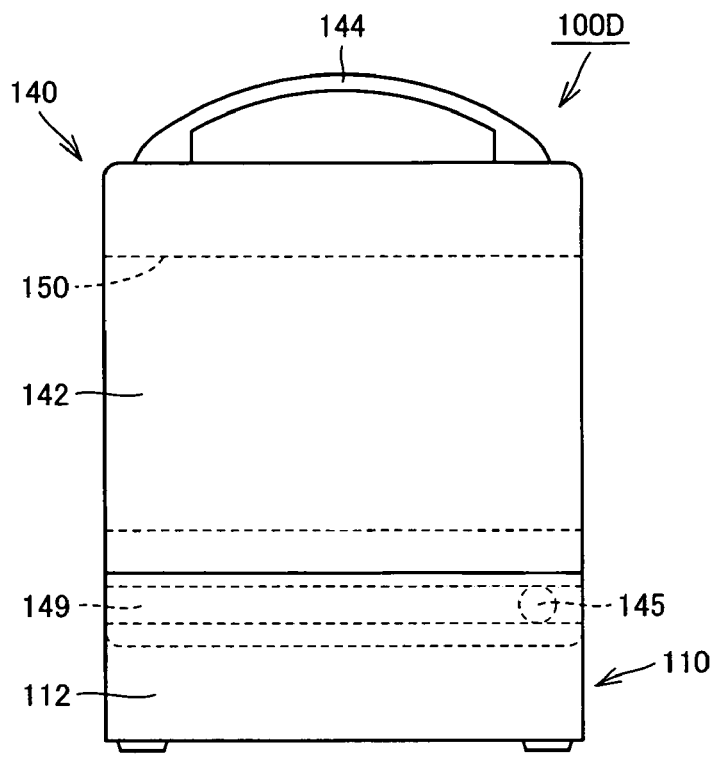
FIGS. 25A and 25B are side views of a blood pressure monitor according to a fourth embodiment of the present invention, in the non-use state and in the use state, respectively.

As shown in FIG. 25A, in the blood pressure monitor 100D of the present embodiment, main unit casing 112 and living body insert portion casing 142 are slidably and pivotally connected via a slide connection mechanism and a pivot connection mechanism. More specifically, the slide connection mechanism is formed, e.g., of a ridge 149 provided at the lower end of living body insert portion casing 142 and a guide groove provided at the upper end of main unit casing 112, and ridge 149 and the guide groove are engaged with each other to connect living body insert portion casing 142 with main unit casing 112 in a slidable manner. Further, the pivot connection mechanism is formed, e.g., of a pivot 145 provided at the rear end of living body insert portion casing 142 and the guide groove of main unit casing 112, and engagement of pivot 145 with the guide groove connects living body insert portion casing 142 with main unit casing 112 in a pivotable manner.

Figure 25B:
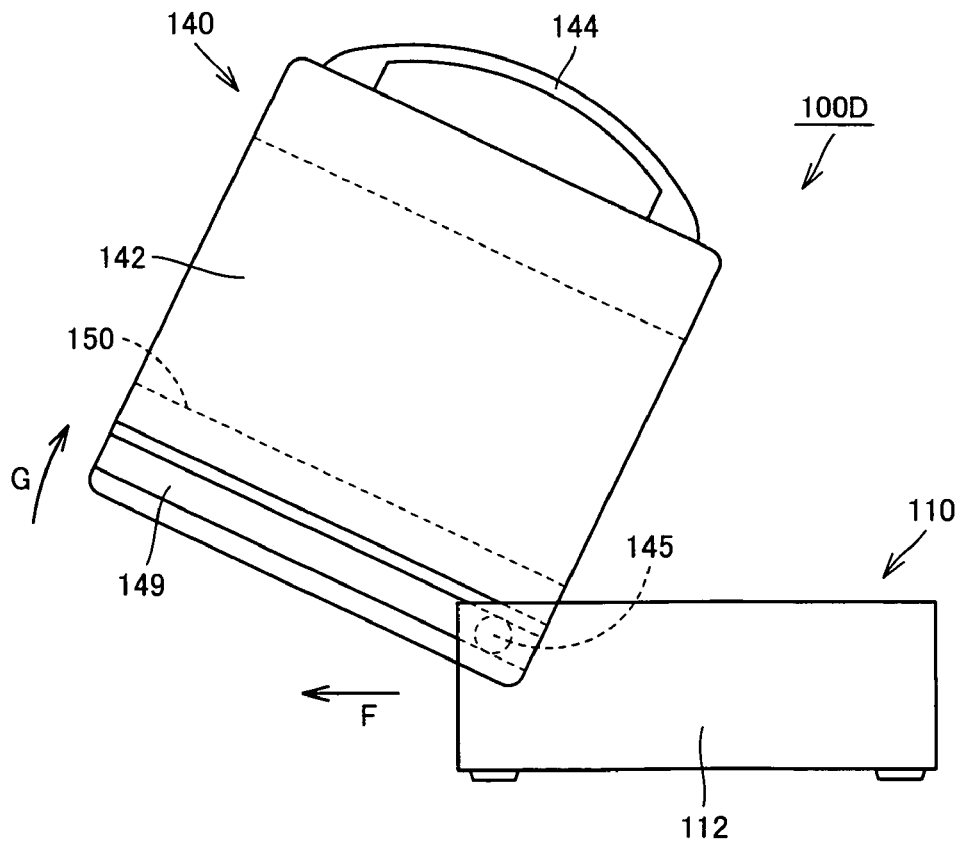
Figure 26:
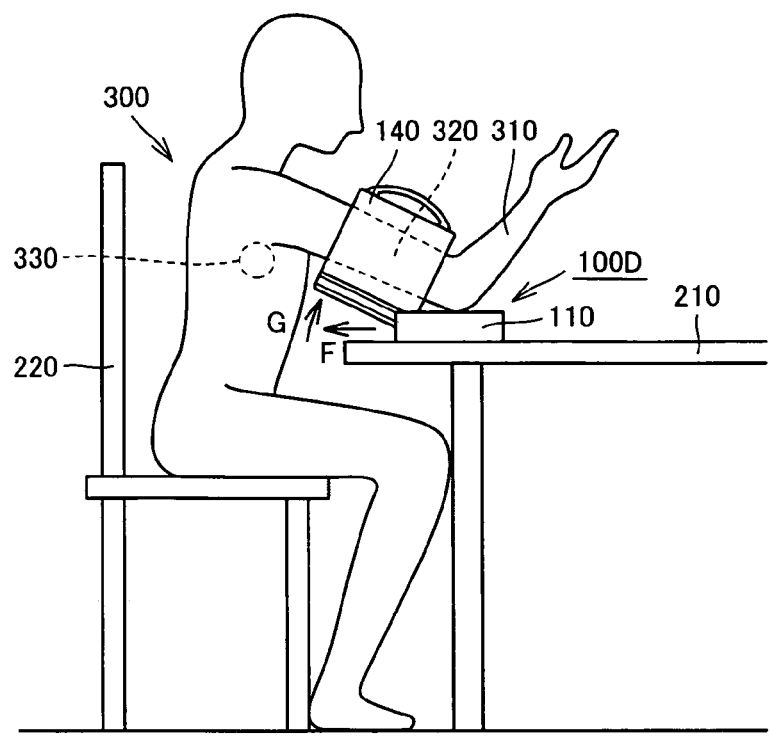
FIG. 26 is a schematic diagram illustrating a posture for measurement when using the blood pressure monitor of the fourth embodiment.
Figure 27:
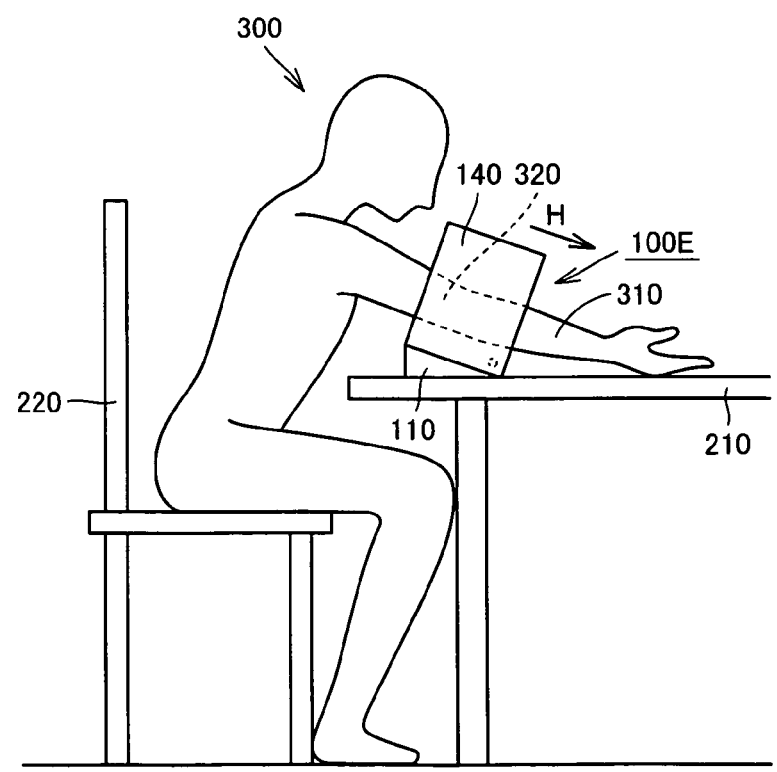
FIG. 27 is a schematic diagram showing a posture for measurement when using a conventional blood pressure monitor.

Upon application of the cuff to the upper arm, as shown in FIG. 25B, living body insert portion casing 142 is moved toward the subject (in the direction shown by an arrow F in the figure) with respect to main unit casing 112, to insert the arm into hollow opening 150 of living body insert portion 140. In the state where the arm is inserted, living body insert portion casing 142 pivotally moves (in the direction shown by an arrow G in the figure) in accordance with the movement of the arm, so that the posture for measurement as shown in FIG. 25B is realized.

With this configuration, the effects similar to those of the first embodiment described above can be obtained. As a result, the subject does not need to suffer unnecessary pain during the measurement, and the measurement can be carried out at a comfortable posture under any conditions. Accordingly, it is possible to accurately and stably measure the blood pressure value.

It is noted that the blood pressure monitor according to the third or fourth embodiment may be provided with the inclination level detecting portion as in the blood pressure monitor of the second embodiment, to make it possible to inform the subject when the inclination level is out of the optimal measurement range and/or to inhibit measurement of the blood pressure at that time.

Further, the blood pressure monitor according to the third or fourth embodiment may also be provided with a dumper, a friction spring, and/or a coil spring or the like to cause the living body insert portion casing to move to a prescribed position when the unlocking button is manipulated, to realize a blood pressure monitor excellent in operability.

In the first through fourth embodiments, the upper arm blood pressure monitor for measuring a blood pressure value by pressing an upper arm has been explained by way of example. The present invention however is of course applicable to a wrist blood pressure monitor. Further, not limited to the blood pressure monitors, the present invention is applicable to a pulse wave detecting device and others as well.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A blood pressure measuring device, comprising:
   a first enclosure adapted for resting on a table;
   a second enclosure located on said first enclosure in a non-use state comprising a casing not capable of being adjusted circumferentially and having a cuff arranged on its inner peripheral surface, the cuff having a hollow opening into which an upper arm of a subject is capable of being inserted in an axial direction of the cuff; and
   a connection mechanism configured for connecting said second enclosure with said first enclosure in a movable manner such that, upon application of said cuff to the subject in a state in which the first enclosure rests on the table, said second enclosure can move to come closer to the subject than in said non-use states,
   wherein one end in an axial direction of a hollow opening of the second enclosure in a non-use state is covered with an upper surface of the first enclosure such that an upper arm cannot be inserted.

2. The blood pressure measuring device according to claim 1, further comprising an inclination level detecting portion for detecting an inclination level of said second enclosure.

3. The blood pressure measuring device according to claim 2, further comprising an informing portion for informing the subject of a result of determination as to whether the inclination level of said second enclosure detected by said inclination level detecting portion is within a predetermined range.

4. The blood pressure measuring device according to claim 2, further comprising a control portion for determining whether the inclination level of said second enclosure detected by said inclination level detecting portion is within a predetermined range, and when it is out of said predetermined range, for controlling to terminate a measurement operation when it is already in progress, and not to enter a measurement operation when it is yet to be started.

5. The blood pressure measuring device according to claim 2, wherein said inclination level detecting portion detects an inclination angle of said second enclosure with respect to a horizontal plane.

6. The blood pressure measuring device according to claim 2, wherein said inclination level detecting portion detects an inclination angle of said second enclosure with respect to said first enclosure.

7. The blood pressure measuring device according to claim 2, wherein said inclination level detecting portion detects an amount of movement of said second enclosure with respect to said first enclosure.

8. The blood pressure measuring device according to claim 1, wherein said connection mechanism is formed of a pivot connection mechanism including a pivot that supports said second enclosure with respect to said first enclosure in a pivotable manner.

9. The blood pressure measuring device according to claim 8, wherein torque required to be applied to said pivot to move said second enclosure is smaller than torque that is imposed on said pivot in accordance with a change in pressure of said cuff during a blood pressure measurement using the cuff.

10. The blood pressure measuring device according to claim 8, wherein said pivot connection mechanism includes at least one of a damper and a friction spring for suppressing abrupt pivotal movement of said second enclosure.

11. The blood pressure measuring device according to claim 8, wherein said pivot connection mechanism further includes a bias portion for biasing said second enclosure in a direction away from said first enclosure in a non-use state, and a locking portion for locking said second enclosure with said first enclosure in opposition to bias force of said bias portion in the non-use state.

12. The blood pressure measuring device according to claim 1, wherein the second enclosure is not rotatable in a left or right direction with respect to the first enclosure when viewed along the axial direction of the cuff.

13. The blood pressure measuring device according to claim 1, wherein the first enclosure includes an elbow rest at an upper surface, and one end in an axial direction of the hollow opening of the second enclosure is covered with said elbow rest in a non-use state.

* * * * *